(12) United States Patent
Lin et al.

(10) Patent No.: US 10,080,595 B2
(45) Date of Patent: Sep. 25, 2018

(54) DEVICE FOR BONE FIXATION

(71) Applicant: Spirit Spine Holdings Corporation, Inc., Pasadena, CA (US)

(72) Inventors: Shih-Hung Lin, Taipei (TW); Shih-Chun Lu, Taipei (TW); Kwan-Ku Lin, Taipei (TW); Shih-Hsiung Hsu, New Taipei (TW)

(73) Assignee: SPIRIT SPINE HOLDINGS CORPORATION, INC., Pasadena, CA (US)

( * ) Notice: Subject to any disclaimer, the term of this patent is extended or adjusted under 35 U.S.C. 154(b) by 1175 days.

(21) Appl. No.: 14/059,981

(22) Filed: Oct. 22, 2013

(65) Prior Publication Data

US 2014/0114368 A1    Apr. 24, 2014

(30) Foreign Application Priority Data

Oct. 23, 2012    (TW) .............................. 101139150 A

(51) Int. Cl.

| A61B 17/88 | (2006.01) |
|---|---|
| A61B 17/70 | (2006.01) |
| A61B 17/72 | (2006.01) |
| A61B 17/74 | (2006.01) |
| A61B 17/16 | (2006.01) |

(52) U.S. Cl.
CPC ...... *A61B 17/7097* (2013.01); *A61B 17/7275* (2013.01); *A61B 17/744* (2013.01); *A61B 17/1668* (2013.01); *A61B 17/8858* (2013.01)

(58) Field of Classification Search
CPC ............ A61B 17/7097; A61B 17/7275; A61B 17/8855; A61B 17/8858
See application file for complete search history.

(56) References Cited

U.S. PATENT DOCUMENTS

| 4,520,821 | A  | * | 6/1985 | Schmidt | ................ | A61F 2/0063 |
|---|---|---|---|---|---|---|
| | | | | | | 435/399 |
| 5,549,679 | A | * | 8/1996 | Kuslich | ................. | A61F 2/0063 |
| | | | | | | 606/247 |
| 7,445,642 | B2 | * | 11/2008 | Amos | ................. | A61M 27/008 |
| | | | | | | 604/8 |
| 2004/0102804 | A1 | * | 5/2004 | Chin | ................ | A61B 17/00008 |
| | | | | | | 606/190 |
| 2006/0106461 | A1 | * | 5/2006 | Embry | ............... | A61B 17/7097 |
| | | | | | | 623/17.12 |
| 2011/0306975 | A1 | * | 12/2011 | Kaikkonen | ........ | A61B 17/7097 |
| | | | | | | 606/63 |

* cited by examiner

*Primary Examiner* — Anu Ramana
(74) *Attorney, Agent, or Firm* — Rabin & Berdo, P.C.

(57) ABSTRACT

A device for bone fixation comprises an expansion part and a covering part. The expansion part has a fixing end and a top end and provides an expansion structure for being adjustable between a state of expansion and contraction. The covering part has a front end and a joining end, wherein the front end thereof is joined to the top end of the expansion part, and the joining end thereof is attached to the fixing end of the expansion part. The covering part is employed to cover the expansion structure. After the expansion part and the covering part are added to the bone, the covering part is unfurled to spread to the expansion state, and the medical filler is injected or pushed into the covering part.

23 Claims, 37 Drawing Sheets

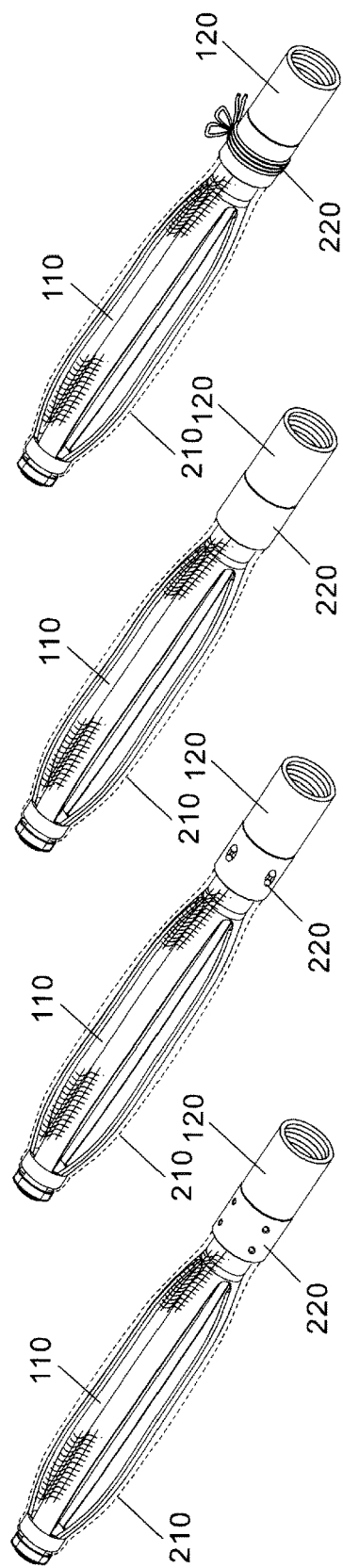

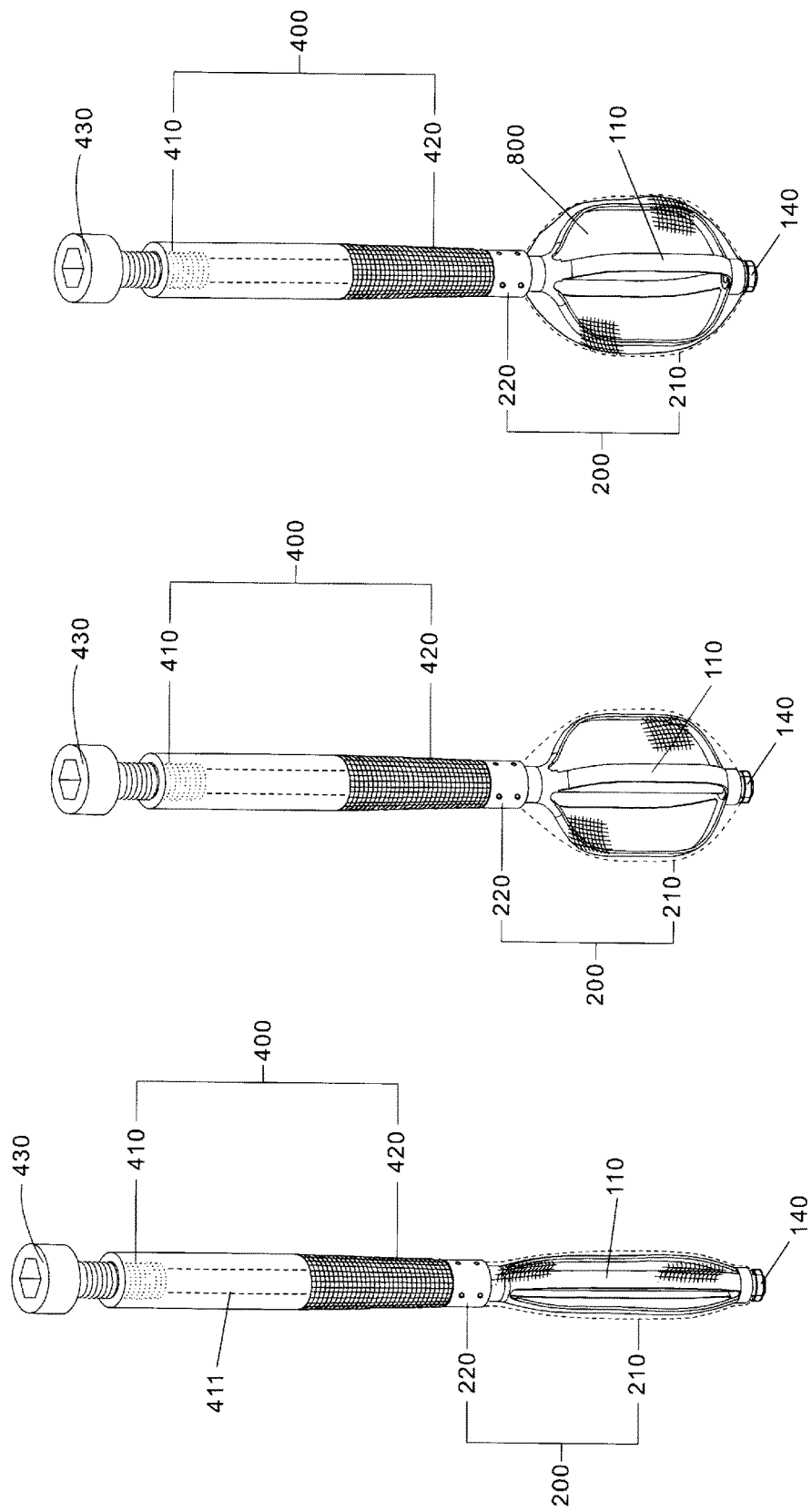

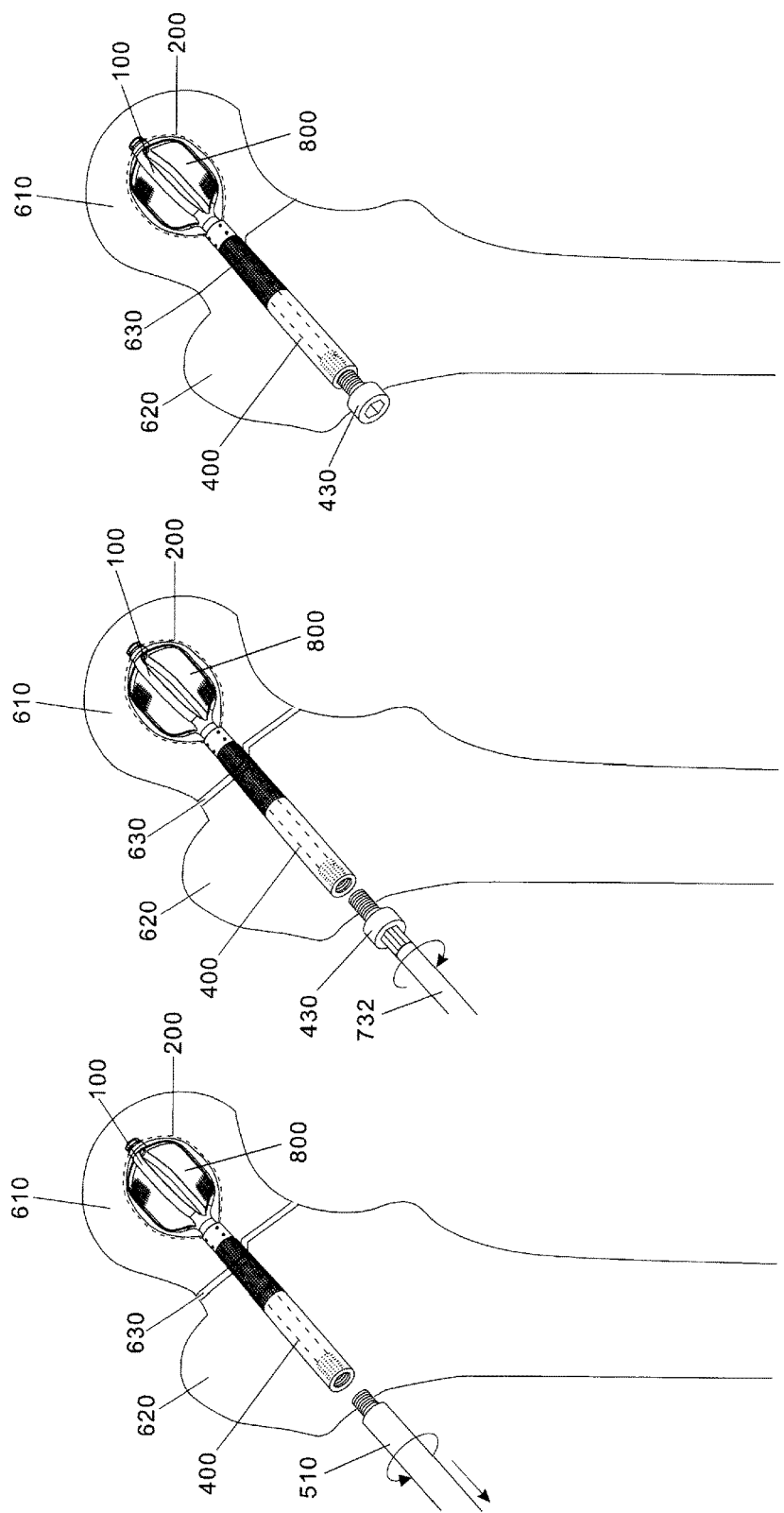

DEVICE FOR BONE FIXATION

FIELD OF THE INVENTION

The present invention relates to a device for bone fixation device, particularly a bone fixation device which comprises an expansion part as well as a covering part.

BACKGROUND OF THE INVENTION

Currently, surgery commonly applied for injecting or filling medical fillers into bones is performed in the following ways:

A mechanical-type hole expansion device, such as is disclosed in U.S. Patent Application Publication Nos. 20110196494, 2011018447, 20100076426, 20070067034, 20060009689, 20050143827, and 20220052623, and U.S. Pat. Nos. 6,354,995, and 6,676,665, is utilized to expand a hole in the bone and create a space, where the hole expansion device is removed after the hole has been bored; a covering device is then inserted before the process of pouring or stuffing medical fillers takes place. This type of surgery has the following shortcoming: The cancellous bone fragments that are crushed by the mechanical-type hole expansion device often fall into the mechanical-type hole expansion device, causing the device to jam and its components unable to be retracted, i.e., unable to be restored to a state of contraction, which in turn causes the entire mechanical-type hole expansion device to become stuck at the location of the hole and unable to be removed.

A filling-type hole expansion device, such as is disclosed in U.S. Pat. Nos. 5,972,015, 6,066,152, 6,235,043, 6,423,083, 6,607,544, 6,623,505, 6,663,646, and 6,716,216, also bores a hole in the bone to create a space, where the hole expansion device is removed after the hole is bored, and a covering device is placed therein, and then the surgery with the pouring or stuffing of the medical filler takes place. Mostly, the filling-type hole expansion device has a balloon (the type of balloon used depends on what is needed) disposed inside the bone with liquid, such as water, poured into the balloon with high pressure, causing the balloon to expand and push away the cancellous bone, achieving the effect of hole expansion. The filling-type hole expansion device also has shortcomings. For example, the balloons used in the process must be attached to a nozzle, which creates the possibility that the balloon may be detached from the nozzle during the high-pressure insertion of liquid into said balloon. There can even be cases where the balloon ruptures.

In the case that a hole expansion process is not done beforehand, and a covering device is placed directly into the bone for the insertion of medical fillers, the hole expansion is instead achieved through the pressure created when medical fillers are inserted into the covering device. In this case the covering device acts as both a hole expansion device and a fixation device as disclosed in, for example, Taiwan patent No. 1321467, Taiwan Patent application publication No. 20112995, and U.S. Pat. No. 6,248,110. It is also possible to exclude a covering device entirely, instead using a perfusion device to directly pour medical filler at the surgery location, such as what U.S. Pat. No. 5,514,137 discloses to reinforce fixation at the surgery location. The surgical way has the following shortcomings: due to the lack of a hole bored before surgery, the area for pouring the medical filler cannot be controlled accurately to cause the direction of the poured medical filler differing from what doctors originally predicted. It can even be the case that, after the medical filler has been poured in, the bone is found to be not completely held up by the covering device, or the medical filler spreads out all over in the bone, or even seeps out of the bone; it might occur that the concentration of slurry-type medical filler is too dilute, or the grains of the medical filler are too fine such that it results in the bone not being successfully held up during the pouring of medical filler, to greatly decrease the originally-expected effectiveness.

A mechanical-type hole expansion device, which is utilized as the bone fixation device such as is disclosed in U.S. patent Application Publication Nos. 20120071977, 20110046739, 20100069913, 20100217335, 20090234395, and 20090005821 is implanted into and props up the bone, with the medical filler being poured immediately afterward to surround the mechanical-type hole expansion device. After pouring, the hole expansion device is left inside the body along with the medical filler. Due to the lack of a covering device, it is not possible to effectively control the flow direction of the medical filler, and the medical filler can therefore spread out in all directions or even flow out of the bone. Besides, the medical filler cannot effectively and fully cover the mechanical-type hole expansion device, and it may follow that the mechanical-type hole expansion device gradually contracts to a state of partly expanding instead of the state of completely expanding. That in turn causes the bone to not be fully propped up, thereby failing to accomplish the original purpose of bone fixation.

The present invention is a bone fixation device which uses a covering part to cover its expansion part. During the hole expansion process, the covering part can effectively prevent any falling of cancellous bone into the expansion part, which allows the expansion part to expand and contract smoothly and repeatedly in the bone to adjust the direction and extent of the hole expansion. In addition, when the medical filler is poured in, the area which poured by the medical filler can be controlled effectively to avoid the medical filler spreading all over in the bone. After pouring is completed, the medical filler can completely cover the expansion part to avoid the expansion part contracting.

SUMMARY OF THE INVENTION

The present invention relates to use of a covering part to cover the expansion part, preventing cancellous bone fragments from falling into the expansion part. The covering part allows the expansion structure to expand and contract smoothly, which is crucial for the expansion structure to repeatedly expand and contract within the bone for hole expansion, in order to control the direction and extent of the hole expansion. The covering part can also effectively control the extent of medical filler pouring, avoiding the medical filler to spreading out within the bone. After completion of medical filler pouring, the medical filler can fully cover the expansion part, avoiding the possibility of said expansion part contracting.

An object of the present invention is to provide a device for bone fixation.

Another object of the present invention is to provide a device for bone fixation with a covering part.

A further object of the present invention is to provide a device for bone fixation with a covering part and an expansion part.

A further object of the present invention is to provide a device for bone fixation with which the medical filler can be stuffed or poured via a tube.

A further object of the present invention is to provide a device for bone fixation which has the capability to prop up a bone.

A further object of the present invention is to provide a device for bone fixation which can prevent bone fragments from jamming the expansion part.

A further object of the present invention is to provide a device for bone fixation with which the medical fillers can fully cover the expansion part.

A further object of the present invention is to provide a device for bone fixation which can cover the expansion part and expand and contract repeatedly.

A further object of the present invention is to provide a device for bone fixation with a pressing device.

A further object of the present invention is to provide a device for bone fixation which has a hollow fixing device.

A further object of the present invention is to provide a device for bone fixation which has limited control over the extent of medical filler pouring.

A device for bone fixation according to the present invention comprises:

an expansion part having an end being a fixing end, and the other end being a top end, and providing an expansion structure for being adjusted between a state of expansion and contraction;

a covering part having a front end; and a joining end, wherein the front end thereof is joined to the top end of the expansion part, and the joining end thereof is fixedly attached to the fixing end of the expansion part, and the covering part is employed to cover the expansion structure;

wherein after the expansion part and the covering part are placed in a bone, the covering part is propped up (e.g., expanded) by the expansion of the expansion structure; and the medical filler is stuffed or poured (e.g., injected or pushed by an injection tool) into the covering part via the fixing end of the expansion part while the expansion structure is in a state of expansion.

The aforementioned expansion structure in the expansion part can be any conventional expansion structure such as is disclosed in U.S. patent Application publication Nos. 20110196494, 20110184447, 20100076426, 20070067034, 20060009689, 20050143827, 20220052623, 6354995, 6676665, 20120071977, 20110046739, 20100069913, 20100217335, 20090234398, and 20090005821, and Taiwan Patent Nos. 585091, and 1318110, wherein it is preferable that the expansion structure is lantern-shape (shown in FIGS. 2a, 2b, 2c, and 2d), or strip shape (shown in 2g, 2h, and 2i).

The aforementioned expansion part is provided with the expansion structure to prop up the covering part in a state of expansion. Thereafter the medical filler is inserted instead of pressure resulting from the medical filler being poured or stuffed into the covering part being used to prop up the covering part. This method avoids the situation that insufficient pressure caused by either slurry medical filler being excessively dilute and seeping out via clearances of the covering part, or the grains of the medical filler being too fine and falling out via clearances of the covering part, is incapable of successfully propping up the expansion structure and the covering part and greatly reduces the required function of the expansion part.

The aforementioned covering part can effectively prevent crushed cancellous bone fragments from jamming in the expansion structure during hole expansion, allowing the expansion structure to repeatedly and smoothly expand and contract, and effectively control the extent of the medical filler pouring to avoid the medical filler spreading out all over within the bone so as not to hurt the patient due to uneven poured medical filler and the medical filler flowing out of the bone. Moreover, after being poured in, the medical filler completely covers the expansion structure to avoid the possibility of the expansion structure to contract.

The front end of the aforementioned covering part can be cylinder-shaped, cone-shaped, sphere-shaped, sphere-like, gourd-shaped, cube-shaped, cube-like or any other conventional shape.

The aforementioned covering part can be any conventional covering device, such as an elastic covering device, a web-shaped covering device, or a porous covering device. The web-shaped covering device or porous covering device is preferable. Additionally, the covering part can be one single or multiple covering devices.

The aforementioned covering part is made of biocompatible material, preferably biocompatible materials that are flexible, such as: PU (poly-urethane), silicone, rubber, or nylon. The covering part can also be a covering device described in other similar devices, such as is disclosed in U.S. Patent Application Publication Nos. 20040122455, 200040210297, 20040073308, 20060149379, and U.S. Pat. No. 6,719,773.

The aforementioned web-shaped covering part can be made of flexible compatible materials, or biocompatible surgery sutures such as catgut and chrome catgut which are made of naturally absorbable sutures, silk and cotton threads which are non-naturally-absorbable sutures, polyglycolic acid threads and poly(lacticacid-co-glycolicacid) ethanol threads which are composite absorbable threads, and nylon threads, polyester fiber threads, polyethelene threads, Polypropylene threads, polydioxanone threads, or polytetrafluoroethylene threads which are composite non-absorbable sutures.

The aforementioned web-shaped covering device can also be made of biocompatible metal wires, such as titanium, titanium alloy, or stainless steel wires.

The top end of the aforementioned expansion part can have a protrusion that holds against the front end of the covering part to protect the covering part from being damaged if the top end of the expansion part is too sharp.

The front end of the aforementioned covering part can also have a protrusion to hold up the projection of the expansion part. The protrusion of the covering part can be slightly thicker than other areas of the covering part to withstand the pressure from the expansion part.

The aforementioned covering part can further include a fixing device joining the protrusion of the expansion part for connection between the expansion part and the covering part to be firmer. Said fixing device can be a collar as shown in FIGS. 5c, and 5d or any other conventional fixing device. The connection between the fixing device and the protrusion of the expansion part can also be implemented by any conventional connection way such as engaging, locking, or binding.

The fixing end of the aforementioned expansion part and the joining end of the covering end can be connected by any conventional connection way, such as riveting, with a retainer ring, locking, adhering, buckling, engaging, or binding. The fixing end of the expansion part can further have a ring-shaped groove, where the covering part can be connected to via riveting, with a retainer ring, locking, adhering or binding. The preferable connection way is the riveting, with a retainer ring, or locking.

The aforementioned device for bone fixation can further include a blocking part which is connected with the fixing end of the expansion part after medical filler has been poured or stuffed inside the bone. This blocking part is used to prevent medical filler from flowing or falling out at the fixing end of said expansion part. The connection between said blocking part and the fixing end of said expansion part can be implemented by any conventional connection way, such as screw threading, engaging, locking, a retainer ring. The preferable connection way is screw threading or engaging.

The aforementioned medical filler can be any conventional medical filler, such as bone grafts, bone substitutes, bone cement, and/or a mixture, composition and composite of the bone grafts, the bone substitutes and the bone cement; Taiwan Patent Application No. 097141700, Taiwan Patent No. 1227146, and U.S. Patent Application Publication No. 20070088436 can be referenced. Generally, the aforementioned medical filler can be simply filled medical filler, such as auto-grafts or allografts which are implanted bone grafts, but the simply filled medical filler has poorer solidifying effects. Therefore, it is preferable that the medical filler is a medical filler paste capable of at least solidifying, such as slurry type medical filler. Alternatively, the transplanted bone grafts can be stuffed and then slurry capable of solidifying can be poured, allowing the slurry to fill up the entire covering part. Generally it is best to use only the slurry medical filler. The slurry type medical filler described here refers to slurry that can be prepared prior to or during its use, and can then solidify within a proper time period after being poured into the covering part. Such medical filler can be bone substitutes, bone cement, and/or a mixture, composition, or composite of both mentioned above. It is preferable that the aforementioned medical filler is osteo-conductive and/or osteo-inductive. Osteo-conductive medical filler can be conventional HA bone filler, while osteo-inductive medical filler can be conventional SrHA medical filler. The osteo-inductive medical filler is preferable, and is described in Taiwan Patent Application No. 097141700. The medical fillers mentioned above are known by persons familiar with the art, and aside from conventional medical fillers, a combination of conventional medical fillers or modified medical fillers can be used. The medical filler can even be any new developed medical filler which has the same effect as described above.

A bone fixation system according the present invention comprises:

a device for bone fixation which further comprises:

an expansion part having an end being a fixing end and another end being a top end, and having an expansion structure which is adjustable between a state of expansion and a state of contraction; and a covering part having an end being a front end and another end being a joining end, wherein the front end of the covering part is joined to the top end of the expansion part, the joining end of the covering part is connected to the fixing end of the expansion part, and the covering part covers the expansion part;

a hollow joining tube having a front end and a rear end, wherein the front end of the hollow joining tube is detachably joined to the fixing end of the expansion part;

an auxiliary expansion part having an end being a coupling end and another end being an operating end, wherein the coupling end is detachably joined to the rear end of said hollow joining tube;

an operation lever having an end being a front end, and another end being a rear end, wherein the front end of the operation lever is detachably joined to said expansion part, the rear end of the operation lever is joined to the operating end of the auxiliary expansion part, and the operation lever is capable of being operated to allow the auxiliary expansion part to adjust the expansion part between a state of expansion and a state of contraction;

an injection tool being joined to the rear end of the joining tube or the rear end of the operation lever to inject or push a medial filler into the covering part via the joining tube or the operation lever;

wherein the auxiliary expansion part is detached and the syringe is attached after the auxiliary expansion part expands the expansion part with the operation lever to fill up the medical filler.

The description of the expansion part, covering part and medical filler is similar to those previously mentioned.

The aforementioned hollow joining tube can be any conventional hollow joining tube.

The aforementioned auxiliary expansion part connecting with the operation lever with the operation lever connecting with the expansion part is capable of adjusting the expansion structure of the expansion part between a state of expansion and a state of contraction; after the expansion part has been expanded, the auxiliary expansion part can be detached and the injection tool can be attached in its place for the insertion of medical filler.

The aforementioned detachable connection can be any conventional detachable connection (as shown in FIGS. 6a, and 6b), such as a connection implemented by engaging, locking, or screw threading.

The detachable connection between the front end of the aforementioned operation lever and the expansion part can be any conventional detachable connection (as shown in FIGS. 7a, 7b, 7c, 7d, and 7e), such as a connection implemented by engaging, locking, or screw threading. The operation lever can be detached and removed from the expansion part through the detachable connection.

The aforementioned operation lever can adjust the expansion structure to a state of expansion or contraction by relative motions of pushing, pulling, or turning (as shown in FIGS. 3a to 3h, 7b, 7c).

The aforementioned operation lever can further be a hollow operation lever which is detached but not completely removed from the expansion part after expanding the expansion structure of the expansion part such that the medical filler is poured or stuffed into the covering part through the hollow operation lever (as shown in FIG. 7e).

The aforementioned hollow operation lever can further be a hollow operation lever with a hole at the front end thereof (as shown in FIGS. 2e, and 2f). After the hollow operation lever has been used to expand the expansion structure, the hole thereof can be used to pour or stuff the medical filler into the covering part, after which it is detached via the detachable connection and removed from the expansion part.

The aforementioned injection tool can be used after the auxiliary expansion part and the operation lever have been detached, wherein e injection tool is attached to the joining tube for injection (as shown in FIG. 1c).

The aforementioned injection tool can, after the removal of the auxiliary expansion part, also be connected with the hollow operation lever for the insertion of medical filler.

The aforementioned bone fixation system can further include one extension tube (as shown in FIG. 1c). The extension tube is used alongside the injection tool to connect to both the rear end of the hollow joint tube and the injection tool. The connection way can be any conventional connection way, such as engaging, locking, or screw threading.

The aforementioned extension tube can be any conventional extension tube.

The aforementioned injection tool can be any conventional injection tool.

The aforementioned bone fixation device can further include a blocking part which is used after the completion of medical filler insertion. The blocking part is connected to the fixing end of the expansion part, and prevents the medical filler from flowing or falling out through the fixing end of the expansion part. The connection way used to connect the blocking part and the expansion part can be any conventional connection way, such as screw threading, engaging, locking, or with a retainer ring. Screw threading or engaging is preferable.

The aforementioned bone fixation system can further include a connection device which can be an engaging groove, a spinal rod, bone hook, bone plate or a combination of these components, as shown in FIGS. 4a, 4b, 4c, 4d, 4e and 15 of Taiwan patent application No. 201039796.

A method of surgery for bone fixation comprises the following steps:

placing a contracted mechanical expansion part into a vertebra with the mechanical expansion part covered by a covering part;

expanding the mechanical expansion device in a state of expansion to prop up the covering part as well as the vertebra;

pouring or stuffing a medical filler into the propped open covering part;

leaving the covering part containing the medical filler and the mechanical expansion part in the vertebra.

The expansion part, covering part, and medical filler are similar to those described previously.

The aforementioned method of bone fixation surgery can further include an auxiliary expansion part, a hollow joining tube, an operation lever, and an injection tool.

The aforementioned device for bone fixation can further include an extension tube.

The auxiliary expansion part, the hollow joining tube, the operation lever, the injection tool and the extension tube are similar to those described previously.

A bone fixation system comprises:

a device for bone fixation which further comprises:

an expansion part having an end being a fixing end and another end being a top end, and having an expansion structure which is adjustable between a state of expansion and a state of contraction; and a covering part having an end being a front end and another end being a joining end, wherein the front end of the covering part is joined to the top end of the expansion part, the joining end of the covering part is secured to the fixing end of the expansion part, and the covering part covers the expansion part;

wherein the expansion part and the covering part are placed in a bone, and the covering part is propped up by said expansion structure to be in the state of expansion;

a hollow fixing device having an end being an injecting end and another end being a connecting end, wherein the connecting end of the hollow fixing device is joined to the fixing end of the expansion part;

a pressing device being joined to the injecting end of the hollow fixing device;

an auxiliary expansion part having an end being a coupling end and another end being an operating end, wherein the coupling end is detachably joined to the injecting end of the hollow fixing device;

an operation lever having an end being a front end, and another end being a rear end, wherein the front end of the operation lever is detachably joined to the expansion part, the rear end of the operation lever is joined to the operating end of the auxiliary expansion part, and the operation lever is capable of being operated to allow the auxiliary expansion part to adjust the expansion part between a state of expansion and a state of contraction;

an injection tool with an end thereof being joined to the injecting end of the hollow fixing device or the rear end of the operation lever to inject or push a medial filler into the covering part via the hollow fixing device or the operation lever;

wherein the auxiliary expansion part is capable of being detached injection tool being attached instead, after the auxiliary expansion part expands the expansion part with the operation lever to fill up the medical filler, and the pressing device is set up after completing filling up the medical filler to press the device for bone fixation toward a bone disposed at a surgery site.

The expansion part, the covering part, the medical filler and operation lever are similar to those described previously.

The aforementioned pressing device can be any conventional pressing device (as shown in FIG. 11), which allows the device for bone fixation to be pressed at the location of the surgery after insertion of the medical filler to reinforce fixing capability of the bone fixation system.

The connection way between the pouring end of the hollow fixing device and the pressing device can be any conventional connection way, such as locking, engaging or screw threading.

The stem of the aforementioned hollow fixing device between the pouring end and connecting end can have various patterns of embossments thereon, such as ring-shaped embossments, stripe-shaped embossments, spot-shaped embossments, or web-shaped embossments. The embossments increase friction between the hollow fixing device and the bone such that it is not easy for the hollow fixing device to slide after surgery. The stem between the pouring end and the connecting end of the hollow fixing device can be provided with holes for the medical filler to be capable of partially flowing out to combine the bone, or for the bone cells to be capable of growing through the holes to combine with the medical filler to enhance the stability between the hollow fixation device and the bone.

The connection way between the connecting end of the hollow fixing device and the fixing end of the expansion part can be any conventional connection way, such as riveting, screw threading, engaging, with retainer rings, or locking.

The aforementioned bone fixation system can further include an auxiliary fixing part (as shown in FIGS. 14, and 15) to increase the stability of the bone fixation system. The auxiliary fixing part can be a bone plate, connecting rods, bone screws, screws, rods, or bone hooks.

The connection between the auxiliary fixing part and the pressing device can be implemented by any conventional connection way, such as joint replacement-screw connection (as shown in FIG. 14), bone plate-bone screw connection, or bone plate-screw connection shown in FIGS. 7a, and 7b in Taiwan patent Application No. 2011112996).

The aforementioned auxiliary expansion part connecting with the operation lever with the operation lever connecting with the expansion part adjusts the expansion structure of the expansion part between a state of expansion and contraction; after the expansion part has been expanded, the auxiliary expansion part can be detached and the injection tool can be attached in its place for the insertion of medical filler.

The connection way between the connecting end of the auxiliary expansion part and the connecting end of the hollow fixing device can be any conventional detachable connection way, such as engaging, locking, or screw threading.

The aforementioned injection tool can be connected to the hollow fixing device for injection after the auxiliary expansion part and the operation lever have been detached.

The aforementioned injection tool also can be connected to the hollow operation lever for insertion of the medical filler after the auxiliary expansion part being detached.

The aforementioned bone fixation system can further include an extension tube which is used alongside the injection tool, where the extension tube is connected to the rear end of the hollow joining tube and the injection tool. The connection way can be any conventional connection way, such as engaging, locking, or screw threading.

The aforementioned extension tube can be any conventional extension tube.

The aforementioned injection tool can be any conventional injection tool.

A method of surgery for bone fixation comprises the following steps:

placing a contracted mechanical expansion part and a hollow fixing device into a bone, wherein the mechanical expansion part is covered by a covering part;

expanding the mechanical expansion device to be in a state of expansion to prop up the covering part;

pouring or stuffing a medical filler into the propped open covering part;

leaving the covering part containing the medical filler, the mechanical expansion part, and the hollow fixing device in the bone;

utilizing a pressing device to allows the hollow fixing device to be pressed at the location of the surgery.

The expansion part, the covering part, the medical filler, the hollow fixing device, and the pressing device are similar to those described previously.

The aforementioned method for bone fixation surgery can further include an auxiliary expansion part, an operation lever, and an injection tool.

The auxiliary expansion part, the operation lever and the injection tool are similar to those described previously.

BRIEF DESCRIPTION OF THE DRAWINGS

The present invention can be more fully understood by reference to the following description and accompanying drawings, in which:

FIGS. 4a, 4b, 4c, and 4d are perspective views illustrating four embodiments of joining ways between the expansion part and the covering part of the device for bone fixation according to the present invention;

FIG. 8a is a perspective view of a preferred embodiment of a system for bone fixation according to the present invention;

FIG. 8b is a perspective view of the preferred embodiment of a bone fixation system in a state of expansion according to the present invention;

FIG. 8c is a perspective view of the preferred embodiment of a bone fixation system in a state of completing injection according to the present invention;

FIGS. 16a to 16k are perspective views illustrating surgery steps of a bone fixation system with the auxiliary fixing device according to the present invention;

DETAILED DESCRIPTION OF THE INVENTION

Figure 1A:
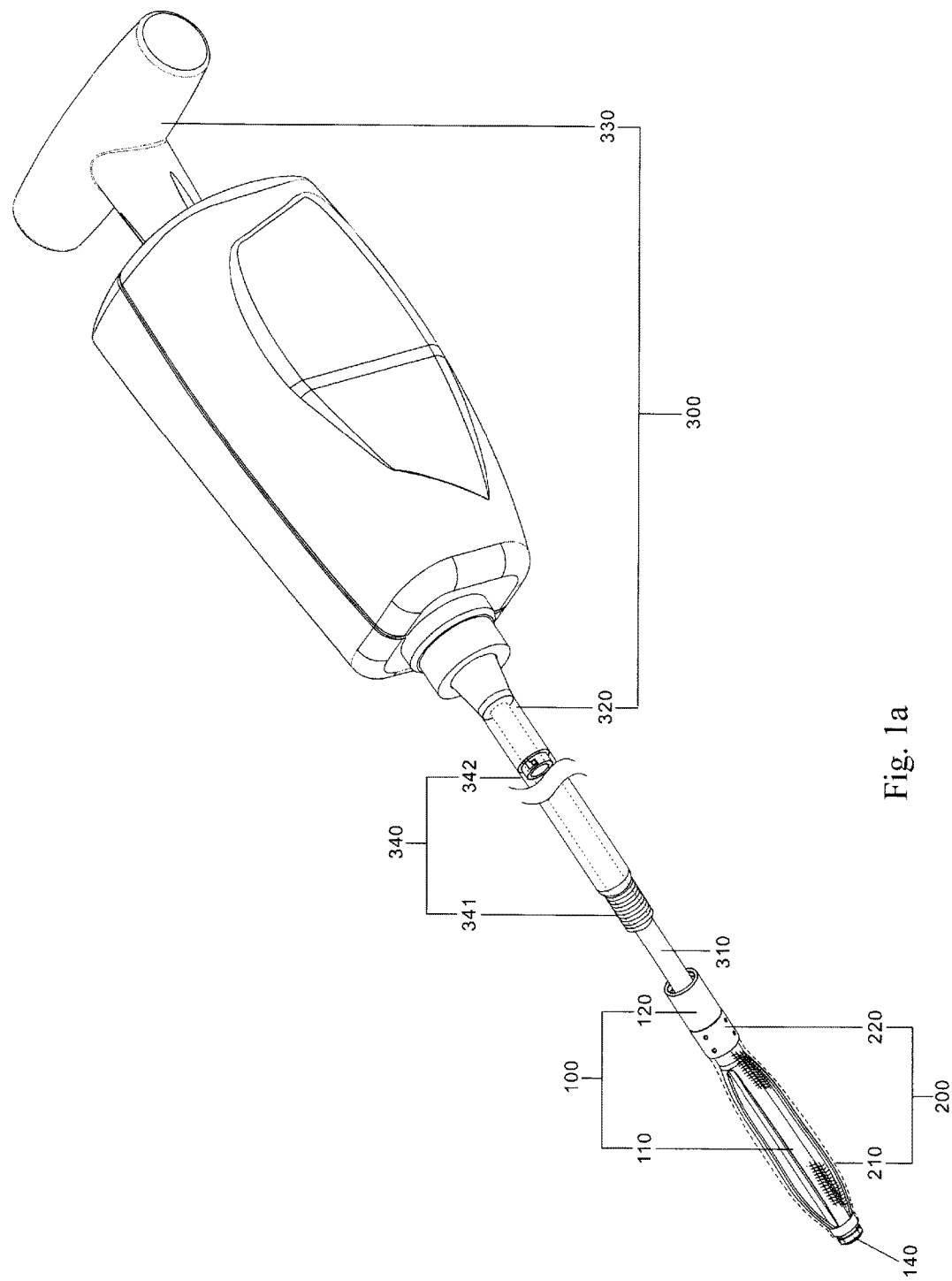
FIG. 1a is a perspective view of a preferred embodiment of a device for bone fixation according to the present invention.

Referring to FIG. 1a illustrates a preferred embodiment of a device for bone fixation according to the present invention. A covering part 200 covers an expansion part 100 with a sphere-like component 210, and, meanwhile, the covering part 200 is capable of blocking off bone fragments in a vertebra to prevent the expansion part 100 from getting stuck caused by the bone fragments in the vertebra and result in the expansion part 100 incapable of contracting to the original state. The covering part 200 is attached to the expansion part 100 with rivets at the joining end 220 thereof. A fixing end 120 of the expansion part 100 and the front end 341 of a joining tube are provided with screw threads to detachably join with each other; an auxiliary expansion part 300 has a joining end 320 to detachably engage with the rear end 342 of the joining tube to facilitate the auxiliary expansion part 300 being replaced with an injection tool for injecting medical filler afterward. An operation lever 310 has an end to detachably join with the front end of the expansion part 100, and another end of the operation lever 310 is joined to an operating end 330 of the auxiliary expansion part 300; the operating end 330 of the auxiliary expansion part 300 is manipulated to move the operation lever 310 so as to allow the operation lever 310 to be capable of controlling expansion or contraction of the expansion structure 110. A fitting piece 140 is employed to reinforce connection between the covering part 200 and the expansion part 100.

Figure 1B:
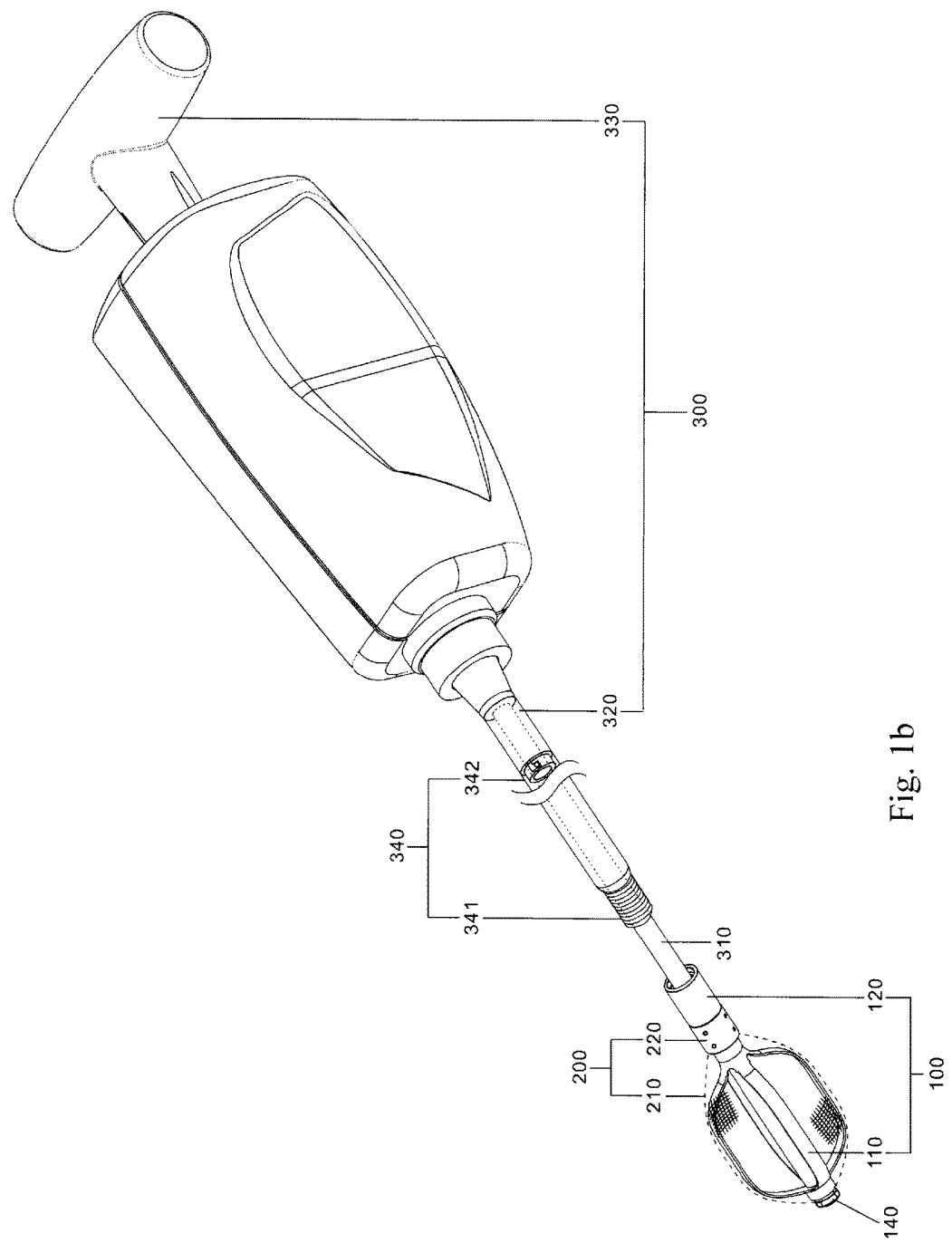
FIG. 1b is a perspective view of a preferred embodiment of a device for bone fixation according to the present invention in a state of expansion.

FIG. 1*b* is a perspective view illustrating the expansion part 100 in a state of expansion.

Figure 1C:
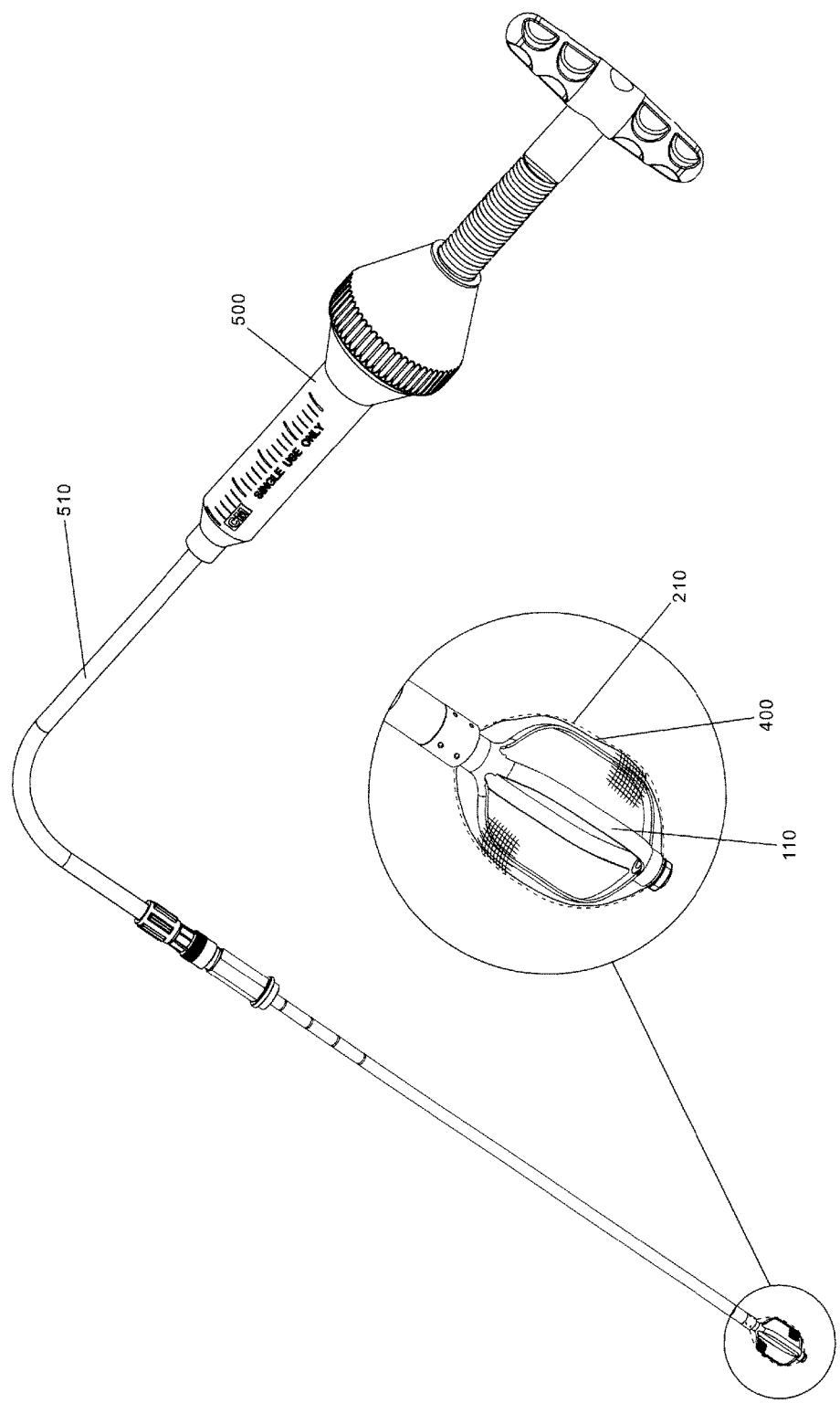
FIG. 1c is a perspective view of a preferred embodiment of a device for bone fixation according to the present invention in a state of injection.

FIG. 1*c* is a perspective view of the preferred embodiment of a device for bone fixation according to the present invention in a state of injection. The fixing end of the expansion part 100 has been connected to an extension tube 510, and the expansion part 100 is detachably connected to the extension tube 510. The expansion part 100 can be detached from the extension tube 510 after the medical filler 800 is completely injected via the injection tool 500 and the extension tube 510.

Figure 2B:
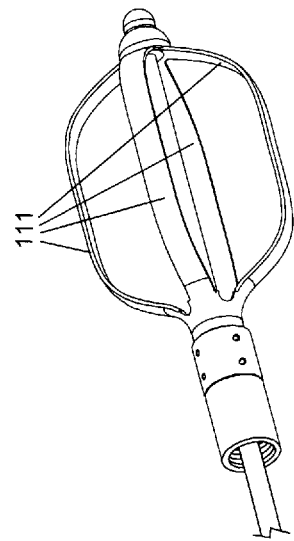
FIGS. 2a, 2b, 2c, 2d, 2e, 2f, 2g, 2h, 2i, 2j, 2k, 2l, 2m, 2n, and 2o are perspective views showing preferred embodiments of the expansion part of the device for bone fixation according to the present invention.
Figure 2A:
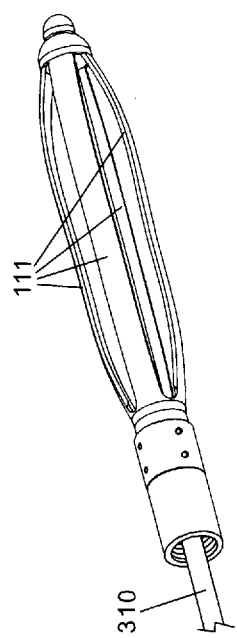
Figure 2D:
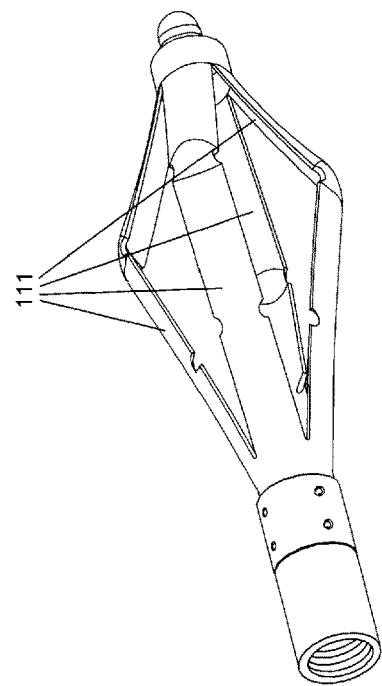
Figure 2C:
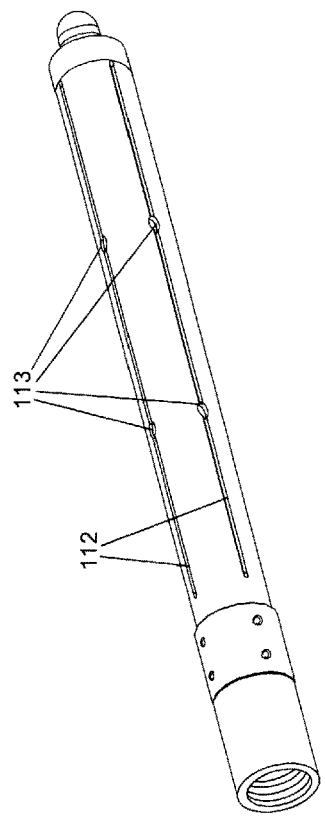
Figure 2F:
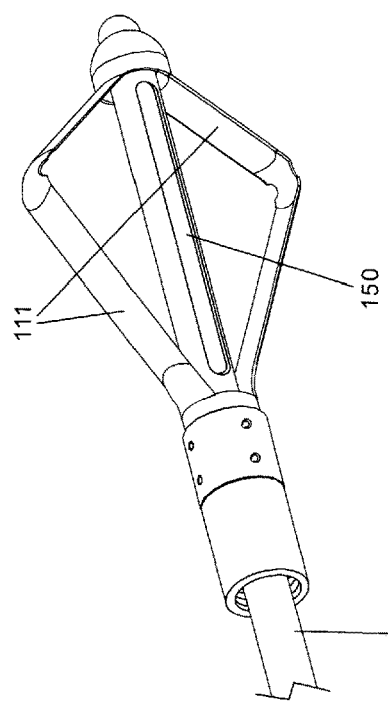
Figure 2E:
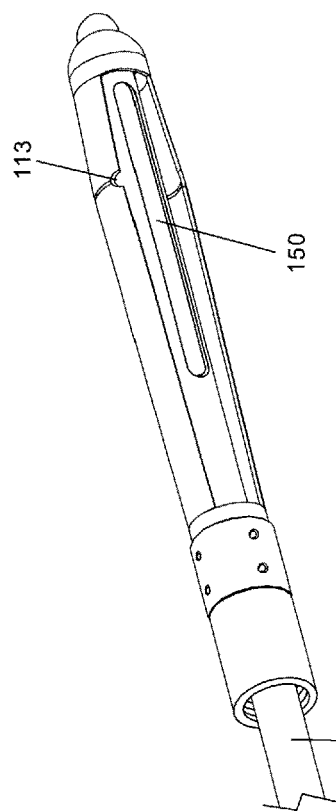
Figure 2I:
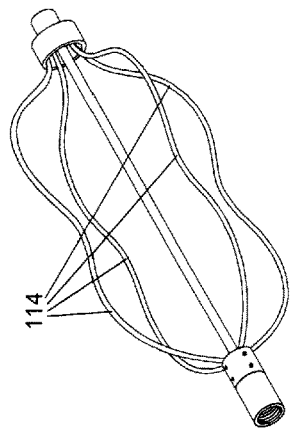
Figure 2H:
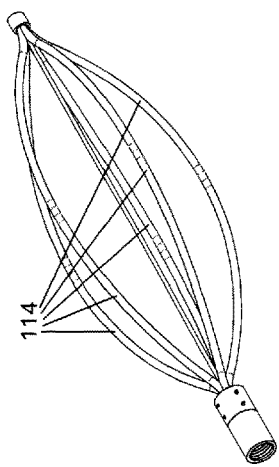
Figure 2G:
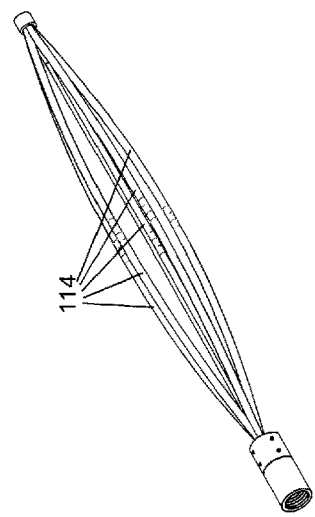
Figure 2K:
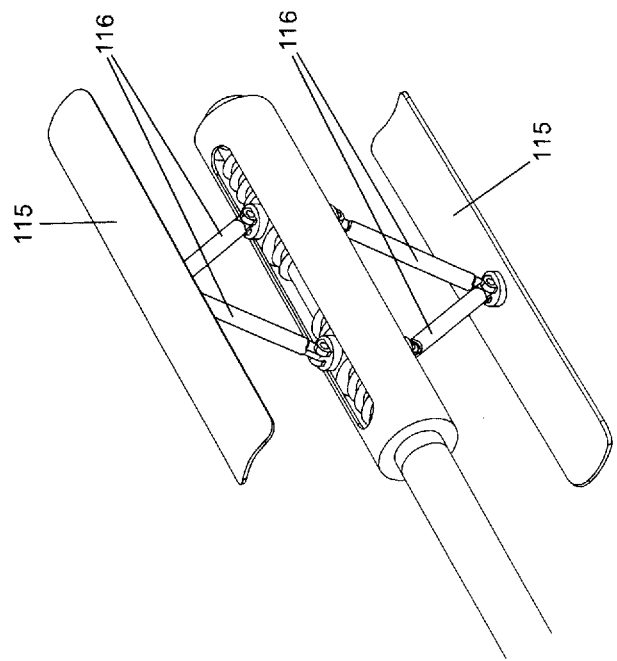
Figure 2J:
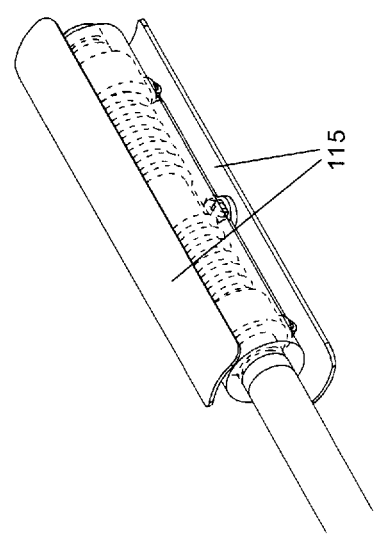
Figure 2M:
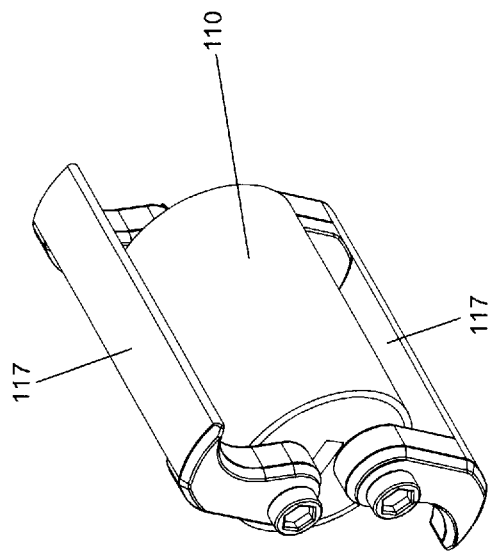
Figure 2L:
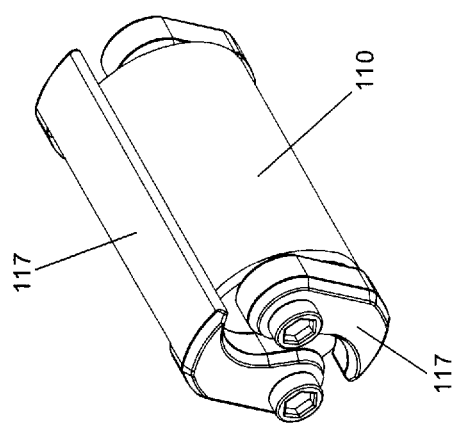
Figure 2O:
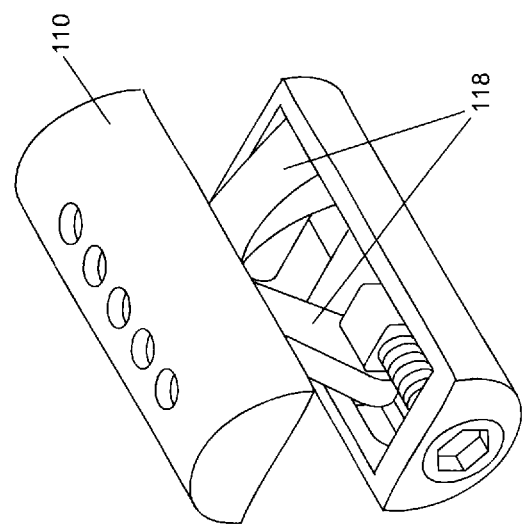
Figure 2N:
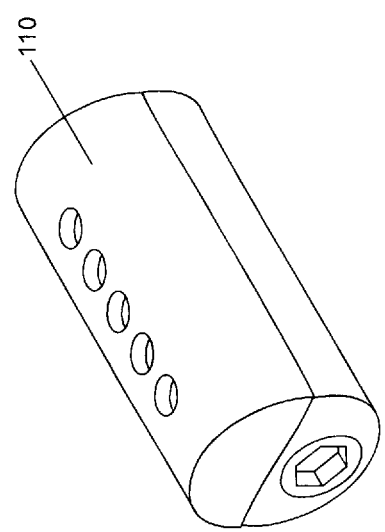

FIGS. 2*a*, 2*b*, 2*c*, 2*d*, 2*e*, 2*f*, 2*g*, 2*h*, 2*i*, 2*j*, 2*k*, 2*l*, 2*m*, 2*n*, and 2*o* are perspective views illustrating preferred embodiments of the expansion part of the device for bone fixation according to the present invention. FIG. 2*a* shows a lantern-shaped expansion structure 111 with four flaps in a state of contraction. FIG. 2*b* shows a lantern-shaped expansion structure 111 with four flaps in a state of expansion. FIG. 2*c* shows another lantern-shaped expansion structure 111 with four flaps in a state of contraction. FIG. 2*d* shows the lantern-shaped expansion structure 111 shown in FIG. 2*c* with four flaps in a state of expansion wherein slits 112 and grooves 113 are utilized. FIG. 2*e* shows a lantern-shaped expansion structure 111 with two flaps in a state of contraction wherein the operation lever 310 has an injecting hole 150 for the medical filler being injected through. FIG. 2*f* shows a lantern-shaped expansion structure 111 with two flaps in a state of expansion wherein the operation lever 310 has an injecting hole 150 for injecting the medical filler. FIG. 2*g* shows an expansion structure 114 with strips in a state of contraction. FIG. 2*h* shows the expansion structure 114 with strips in a state of expansion. FIG. 2*i* shows the expansion structure 114 with strips made of shape memory metal forming a gourd shape. FIG. 2*j* shows an expansion structure 115 with plates in a state of contraction. FIG. 2*k* shows the expansion structure 115 with plates in a state of expansion wherein expansion rods 116 are employed to prop up the expansion structure 115 to the expansion state. FIG. 2*l* shows a leaf-shaped expansion structure 117 in a state of contraction. FIG. 2*m* shows the leaf-shaped expansion structure in a state of expansion. FIG. 2*n* shows an expansion structure 110 in a state of contraction. FIG. 2*o* shows the expansion structure 110 is propped up to a state of expansion with rod members 118.

Figure 3A:
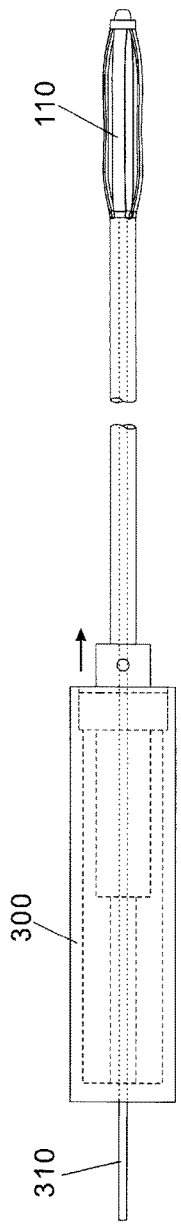
FIGS. 3a, 3b, 3c, 3d, 3e, 3f, 3g, and 3h are perspective views illustrating four different expansion ways of the device for bone fixation according to the present invention.
Figure 3B:
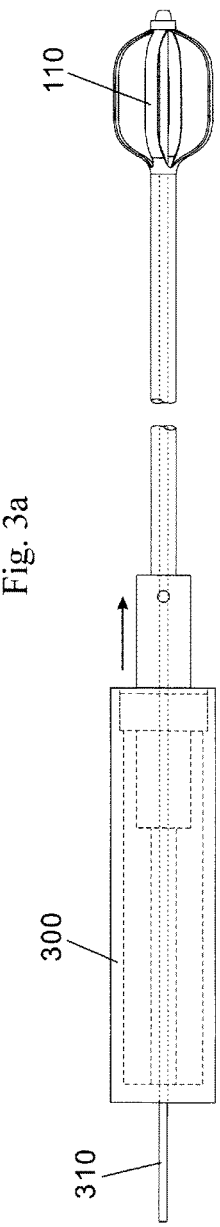
Figure 3C:
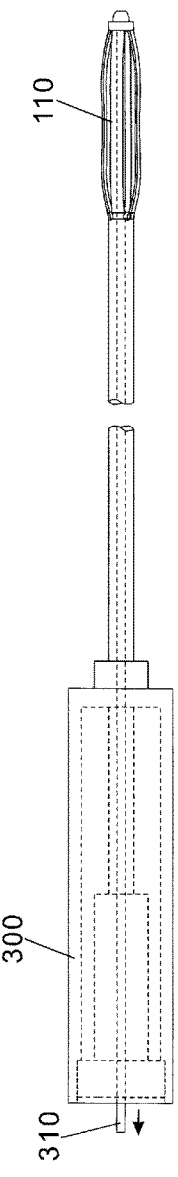
Figure 3D:
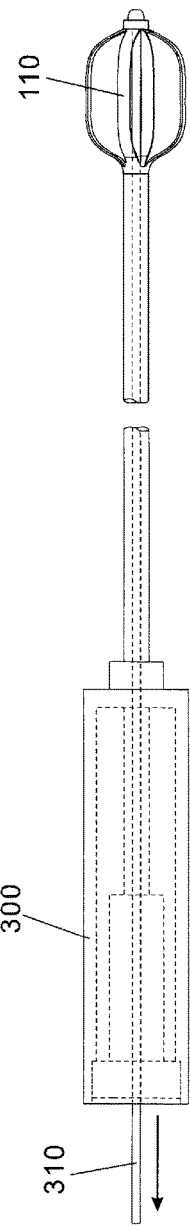
Figure 3F:
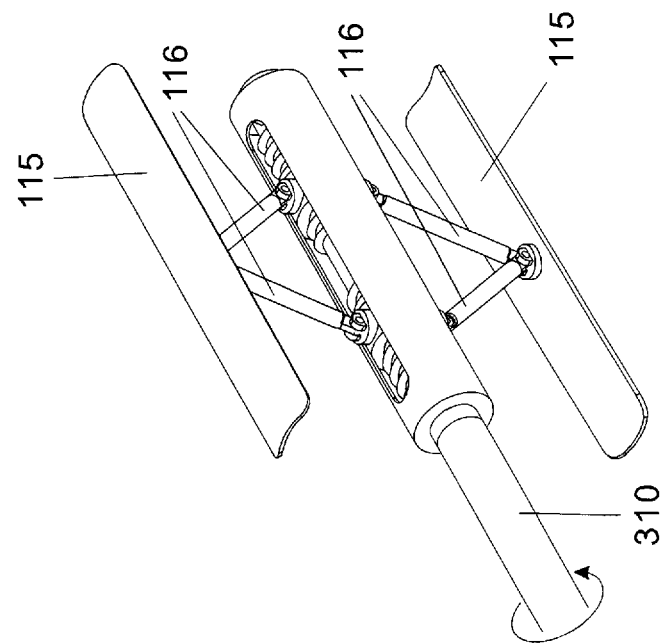
Figure 3E:
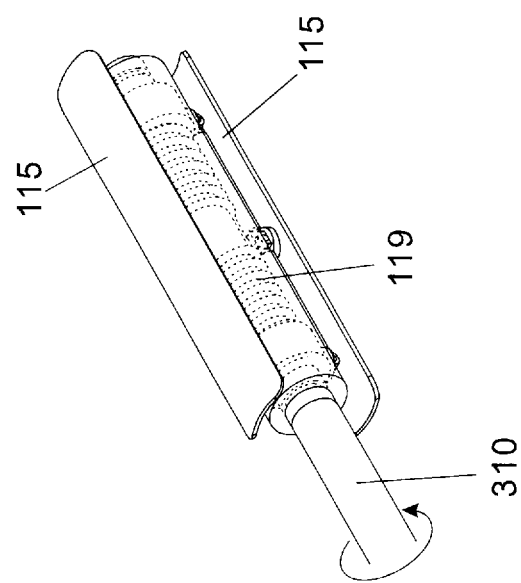
Figure 3H:
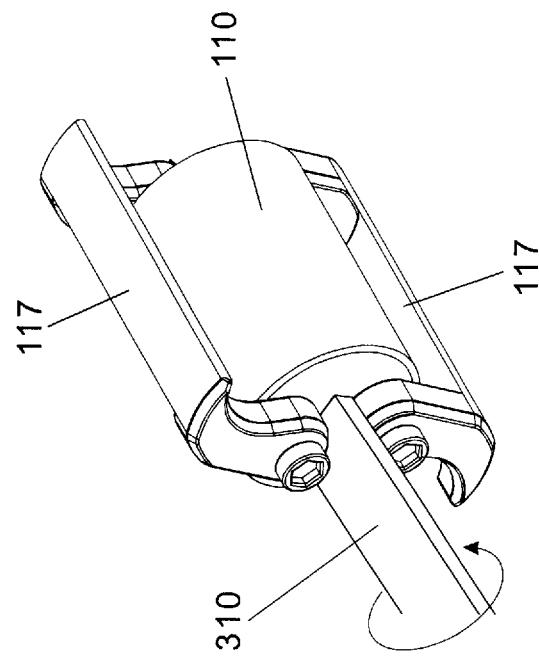
Figure 3G:
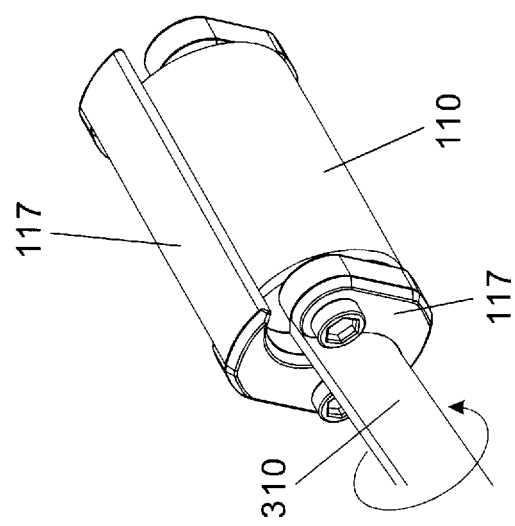

FIGS. 3*a*, 3*b*, 3*c*, 3*d*, 3*e*, 3*f*, 3*g*, and 3*h* illustrate four different expansion ways of the device for bone fixation according to the present invention. FIGS. 3*a* and 3*b* show that the operation lever 310 is pushed to change the expansion structure 110 from the contraction position to the expansion position. FIGS. 3*c* and 3*d* show that the operation lever 310 is pulled to change the expansion structure 110 from the contraction position to the expansion position. FIGS. 3*e* and 3*f* show that the operation lever 310 is rotated and screw threads 119 are utilized to extend the expansion rods 116 so as to change the plate-shaped expansion structure from the contraction position to the expansion position. FIGS. 3*g* and 3*h* show that the operation lever 310 is rotated to change the leaf-shaped expansion structure 117 from the contraction position to the expansion position.

FIGS. 4*a*, 4*b*, 4*c*, and 4*d* illustrate four embodiments of joining ways between the expansion part and the covering part of the device for bone fixation according to the present invention. FIG. 4*a* shows that the fixing end of the expansion part 120 is joined to the joining end 220 of the covering part 220 with riveting. FIG. 4*b* shows that the fixing end of the expansion part 120 is joined to the joining end 220 of the covering part 220 with locking. FIG. 4*c* shows that the fixing end of the expansion part 120 is joined to the joining end 220 of the covering part 220 with fitting. FIG. 4*d* shows that the fixing end of the expansion part 120 is joined to the joining end 220 of the covering part 220 with binding.

Figure 5B:
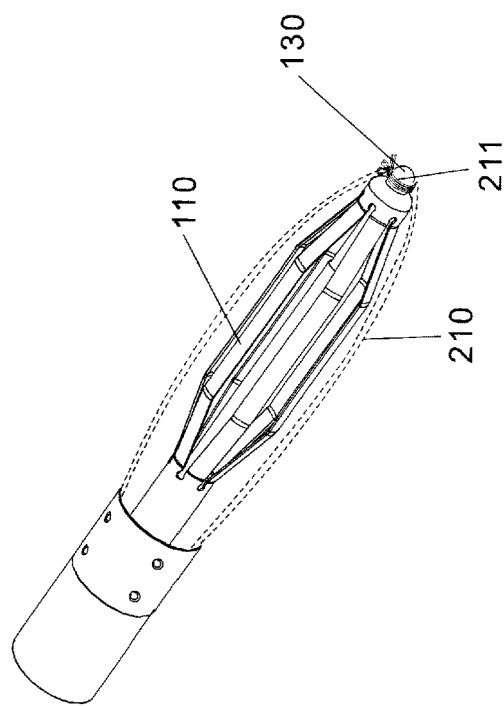
FIGS. 5a, 5b, 5c, and 5d are perspective views illustrating two embodiments for the expansion part joining with the covering part of the device for bone fixation according to the present invention.
Figure 5A:
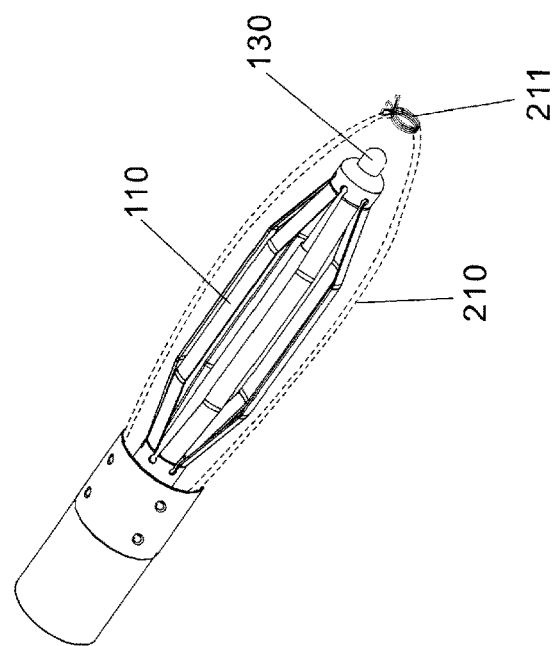
Figure 5D:
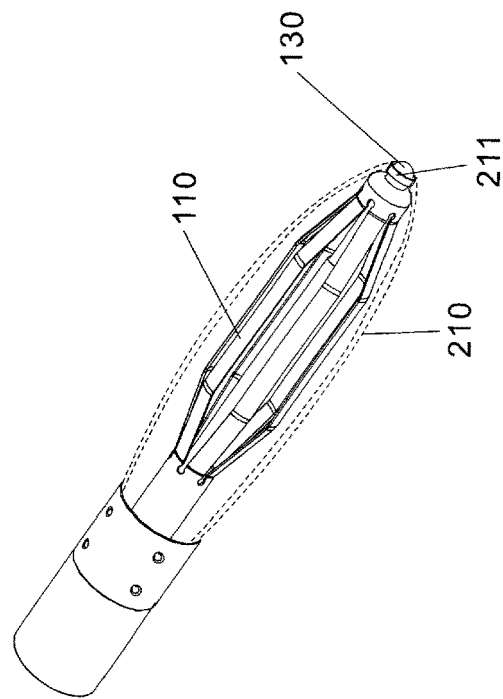
Figure 5C:
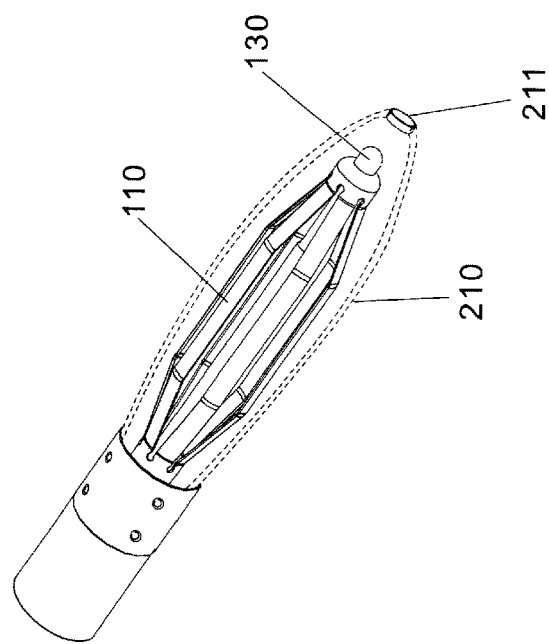

FIGS. 5*a*, 5*b*, 5*c*, and 5*d* illustrate two embodiments for the expansion part joining with the covering part of the device for bone fixation according to the present invention. FIGS. 5*a* and 5*b* show that a sphere-like double-layer covering member 210 is fixed to a protrusion 130 of the expansion part with binding of a fixing member 211. FIGS. 5*c* and 5*d* show that a sphere-like double-layer covering member 210 is fixed to a protrusion 130 of the expansion part with a fixing member 211.

Figure 6B:
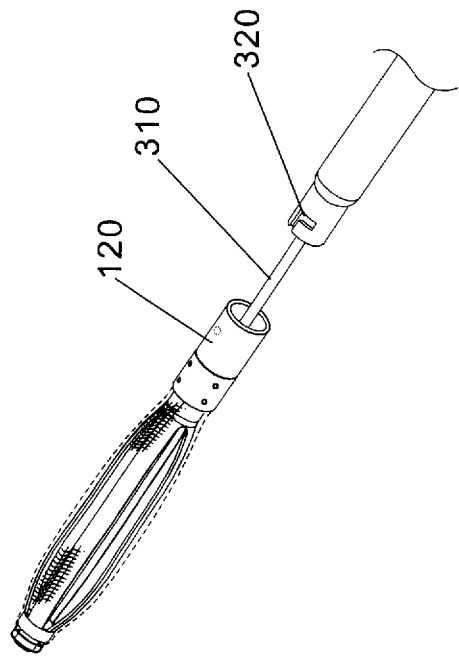
FIGS. 6a, and 6b are perspective views illustrating two embodiments of a joining structure between the expansion part and an auxiliary expansion part of the device for bone fixation according to the present invention.
Figure 6A:
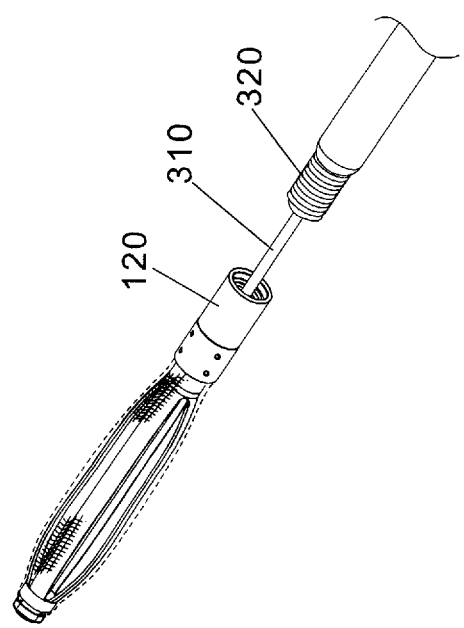

FIGS. 6*a* and 6*b* illustrate two embodiments of a joining structure between the expansion part and an auxiliary expansion part of the device for bone fixation according to the present invention. FIG. 6*a* shows the fixing end 120 of the expansion part is detachable to engage with the joining end 320 of the auxiliary expansion part with screw threads. FIG. 6*b* shows the fixing end 120 of the expansion part is detachable to join with the joining end 320 of the auxiliary expansion part with locking.

Figure 7A:
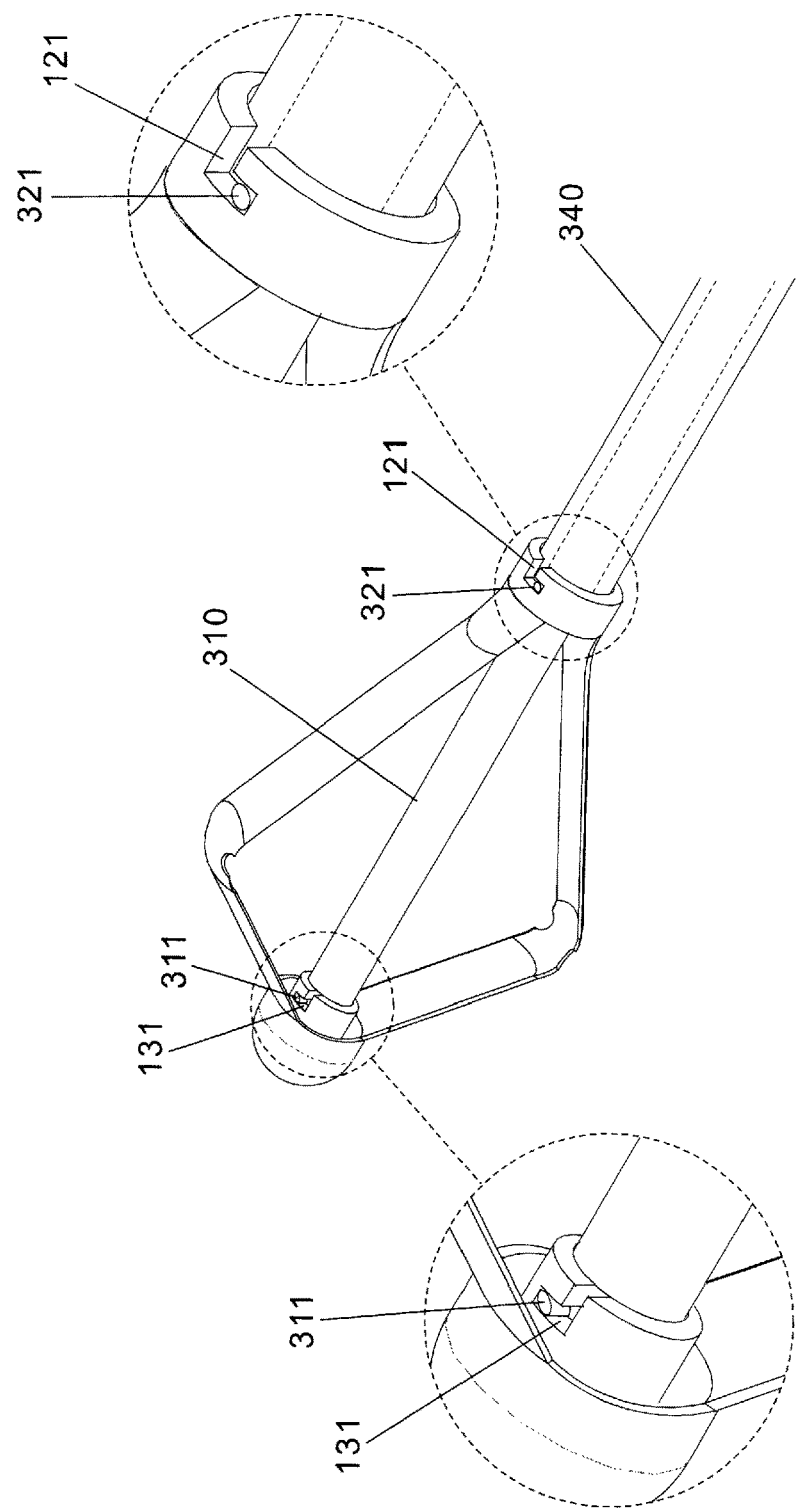
FIG. 7a is a perspective view.
Figure 7C:
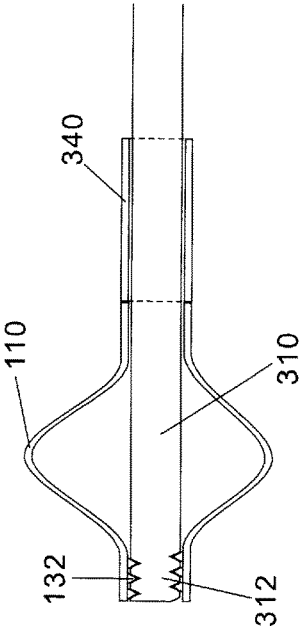
FIGS. 7b, 7c, 7d and 7e are plan views to illustrate two examples of joining structures between the expansion part and an operating shaft of an auxiliary expansion part of the device for bone fixation according to the present invention.
Figure 7B:
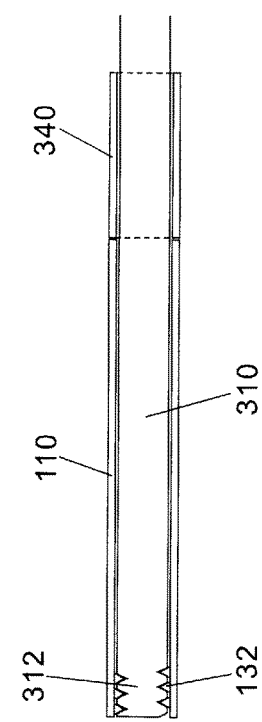
Figure 7E:
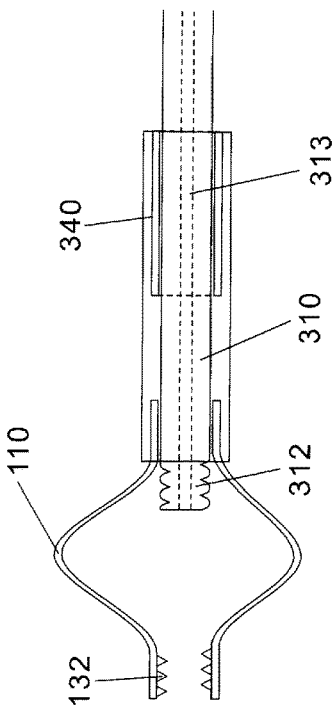
Figure 7D:
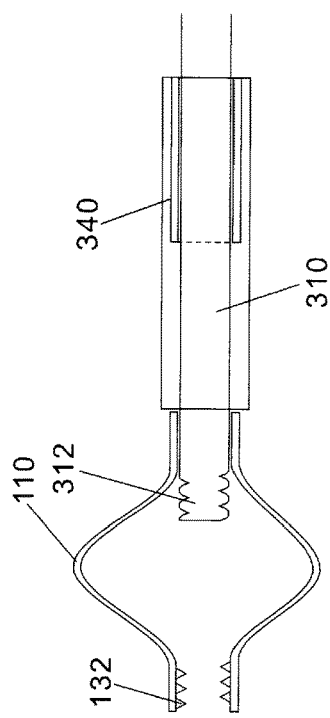

FIGS. 7*a*, 7*b*, 7*c* and 7*d* illustrate two embodiments of joining structures between the expansion part and an operating shaft of the auxiliary expansion part of the device for bone fixation according to the present invention. FIG. 7*a* shows a locking groove 131 disposed at the top of the expansion part and a locking protrusion piece 311 of the operation lever 310 forming detachable engagement; the operation lever 310 is detached and replaced with the injection tool after the expansion part is expanded by the operation lever 310. The stem 340 of the auxiliary expansion part also has a locking protrusion piece 321 to detachably lock with the retaining groove 121 of the expansion part as well. FIGS. 7*b* to 7*e* show that with an upper screw threads 312 engaging with screw threads 132 at the top end of the expansion structure 110, the operation lever 310 is capable of being controlled to expand the expansion structure 110; the operation lever 310 is withdrawn from the expansion structure 110 after the manipulation of expansion is completed. The operation lever 310 shown in FIG. 7*e* has a hollow passage 313 for injecting the medical filler.

FIG. 8*a* illustrates a preferred embodiment of a bone fixation system according to the present invention. A hollow fixing device 400 is joined to the expansion part with rivets, and the stem 420 of the hollow fixing device 400 is embossed thereon to enhance friction between the hollow fixing device 400 and the bone such that it is not easy for the hollow fixing device 400 to slide after surgery. There is an injection passage 411 in the hollow fixing device 400 for the medical filler, and a pressing device 430 is attached to the hollow fixing device 400 for the expansion part capable of pressing the bone located at the surgery site after the medical filler is injected completely.

FIG. 8*b* illustrates the expansion structure in FIG. 8*a* in a state of expansion.

FIG. 8*c* illustrates the expansion structure shown in FIG. 8*b* after the medical filler is injected completely.

Figure 9E:
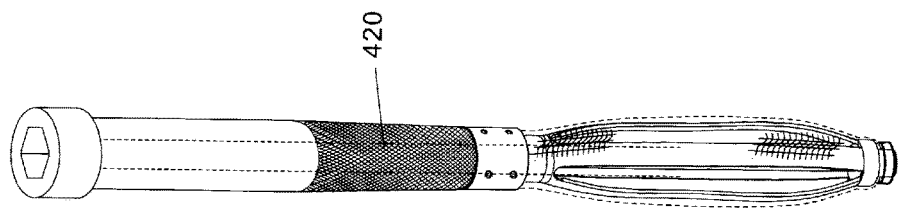
FIGS. 9a, 9b, 9c, 9d, and 9e are perspective views of five preferred embodiments of the hollow fixation device of a bone fixation system according to the present invention without or with an embossed outer surface on the hollow fixing device.
Figure 9D:
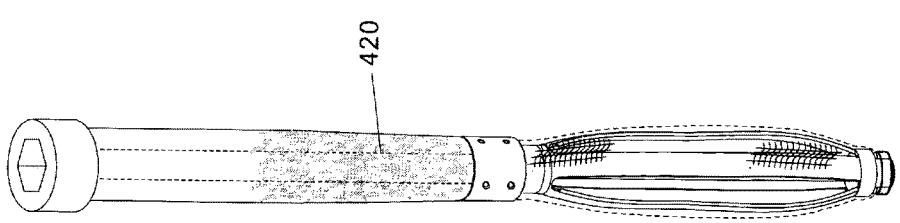
Figure 9C:
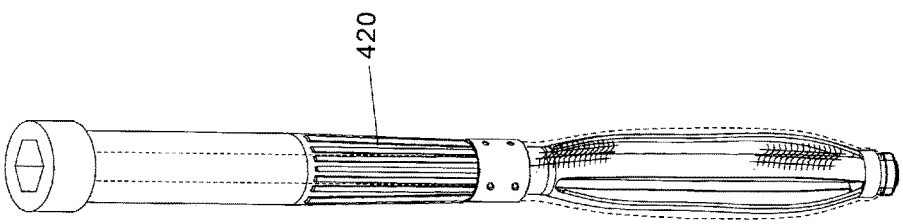
Figure 9B:
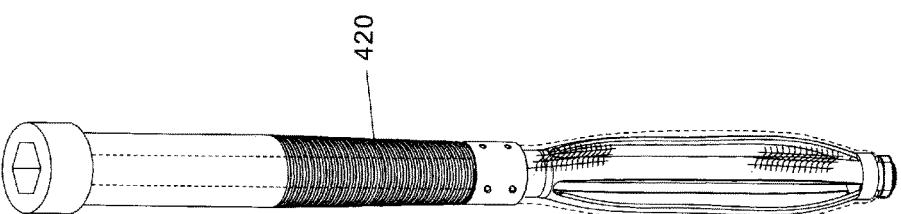
Figure 9A:
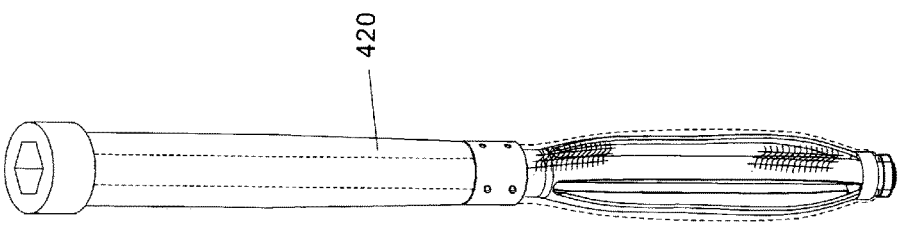

FIGS. 9*a*, 9*b*, 9*c*, 9*d*, and 9*e* illustrate five preferred embodiments for embossment on the stem 420 of the hollow fixing device of a bone fixation system according to the present invention. FIG. 9*a* shows that there is no embossment on the stem 420 of the hollow fixing device. FIG. 9*b* shows that the stem 420 of the hollow fixing device has ring-shaped embossments. FIG. 9*c* shows that the stem 420 of the hollow fixing device has stripe-shaped embossments. FIG. 9*d* shows that the stem 420 of the hollow fixing device has spot-shaped embossments. FIG. 9*e* shows that the stem 420 of the hollow fixing device has net-shaped embossments.

Figure 10B:
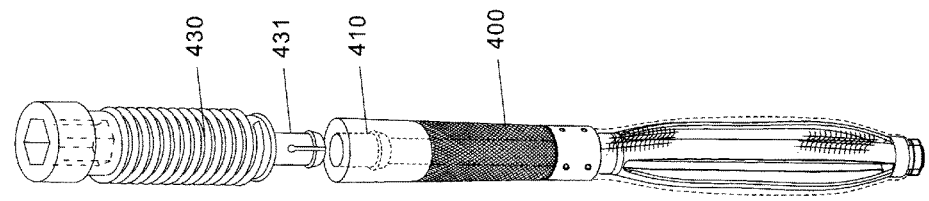
FIGS. 10a, and 10b are perspective views illustrating two types of engaging parts joining the hollow fixing device of a bone fixation system according to the present invention.
Figure 10A:
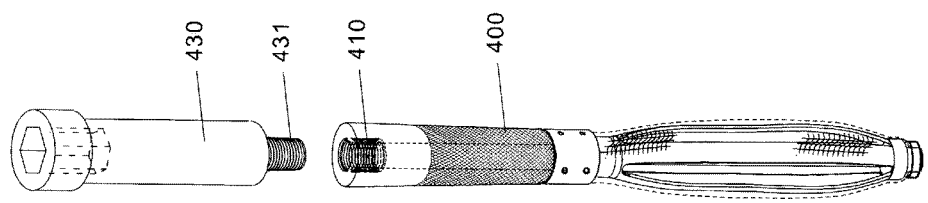

FIGS. 10*a* and 10*b* illustrate two embodiments for the pressing device joining the hollow fixing device of a bone fixation system according to the present invention. FIG. 10*a* shows that the joining end 431 of the pressing device is joined to the injection end 410 of the hollow fixing device 400 with screw threads. FIG. 10*b* shows that the joining end 431 of the pressing part fits with the injection end 410 of the hollow fixing device 400.

Figure 11:
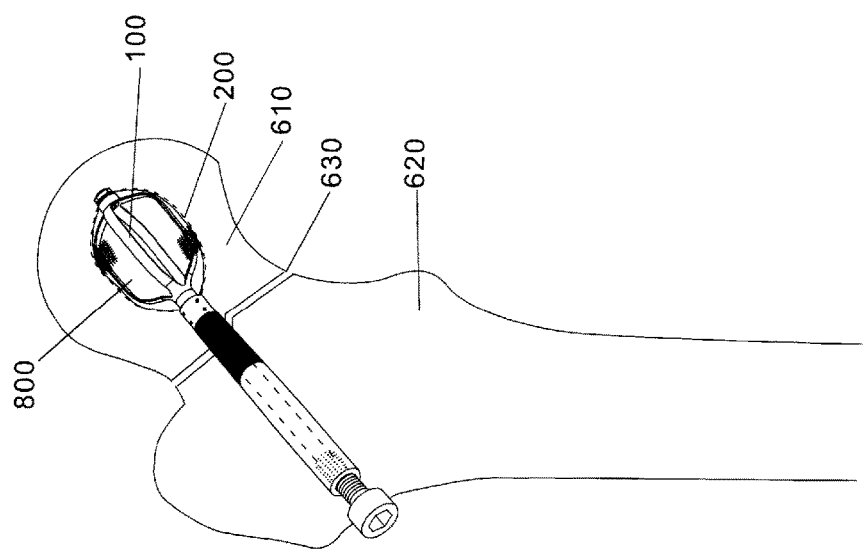
FIG. 11 is a perspective view illustrating a bone fixation system according to the present invention applied to a hip joint.

FIG. 11 illustrates a preferred embodiment of a bone fixation system according to the present invention applied to a hip joint. The hollow fixing device 400, the expansion part 100, and the covering part 200 pass through a rear broken bone 620, a crack 630, and a front broken bone 610, and the front broken bone 610 and the rear broken bone 620 are joined to each other via injection of the medical filler 800; further, the pressing device 430 is utilized to unite the front broken bone 610, the rear broken bone 620, and the hollow fixing device 400 more closely to enhance firmness thereof. Steps of surgery for bone fixation are shown in FIGS. 16*a* to 16*k*.

Figure 12:
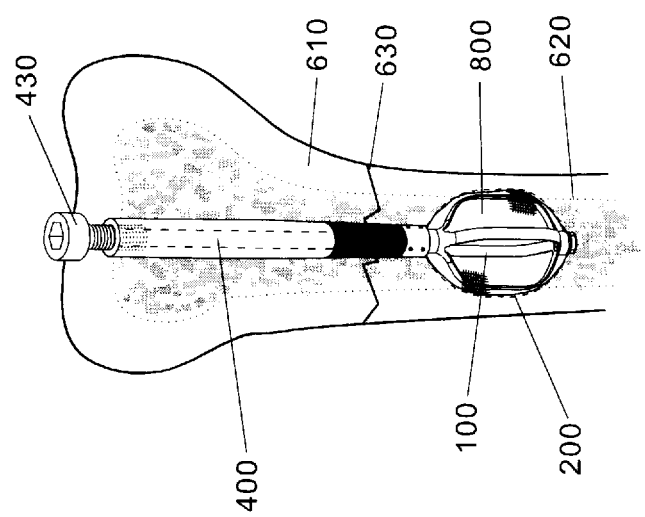
FIG. 12 is a perspective view illustrating a bone fixation device according to the present invention applied to a long bone.

FIG. 12 illustrates a preferred embodiment of a system for bone fixation according to the present invention applied to a long bone. The hollow fixing device 400, the expansion part 100, and the covering part 200 pass through a rear broken bone 620, a crack 630, and a front broken bone 610, and the front broken bone 610 and the rear broken bone 620 are joined to each other via injection of the medical filler 800; further, the pressing device 430 is utilized to unite the front broken bone 610, the rear broken bone 620, and the hollow fixation device 400 more closely to enhance firmness thereof. Steps of surgery for bone fixation can be seen in FIGS. 16*a* to 16*k*.

Figure 13:
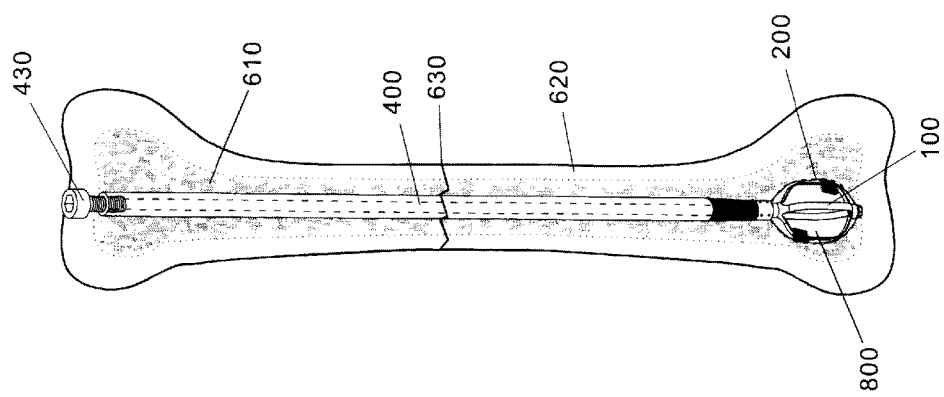
FIG. 13 is another perspective view illustrating a bone fixation system according to the present invention applied to a long bone.

FIG. 13 is another embodiment for a bone fixation system according to the present invention applied to a long bone. The hollow fixing device 400, the expansion part 100, and the covering part 200 pass through a rear broken bone 620, a crack 630, and a front broken bone 610, and the front broken bone 610 and the rear broken bone 620 are joined to each other via injection of the medical filler 800; further, the pressing device 430 is utilized to unite the front broken bone 610, the rear broken bone 620, and the hollow fixing device 400 more closely to enhance firmness thereof. Steps of surgery for bone fixation can be seen in FIGS. 16*a* to 16*k*.

Figure 14:
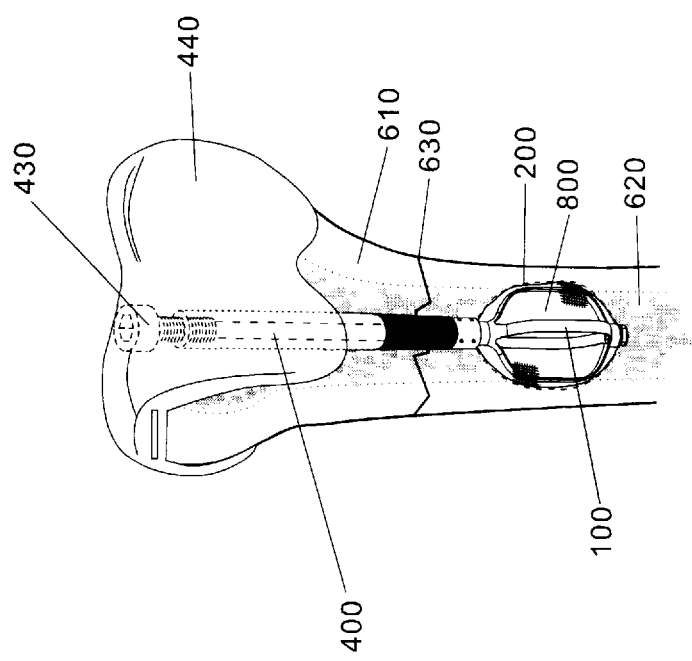
FIG. 14 is a perspective view illustrating a bone fixation system with an auxiliary fixing device according to the present invention applied to a long bone.

FIG. 14 illustrates a bone fixation system with an auxiliary fixing device according to the present invention applied to a long bone. The hollow fixing device 400, the expansion part 100, and the covering part 200 pass through a rear broken bone 620, a crack 630, a front broken bone 610 and an auxiliary fixing part 440. The front broken bone 610 and the rear broken bone 620 are joined to each other via injection of the medical filler 800; further, the pressing device 430 is utilized to unite the front broken bone 610, the rear broken bone 620, the hollow fixing device 400 and the auxiliary fixing device 440 more closely to enhance firmness thereof. Steps of surgery for bone fixation can be seen in FIGS. 16*a* to 16*k*.

Figure 15:
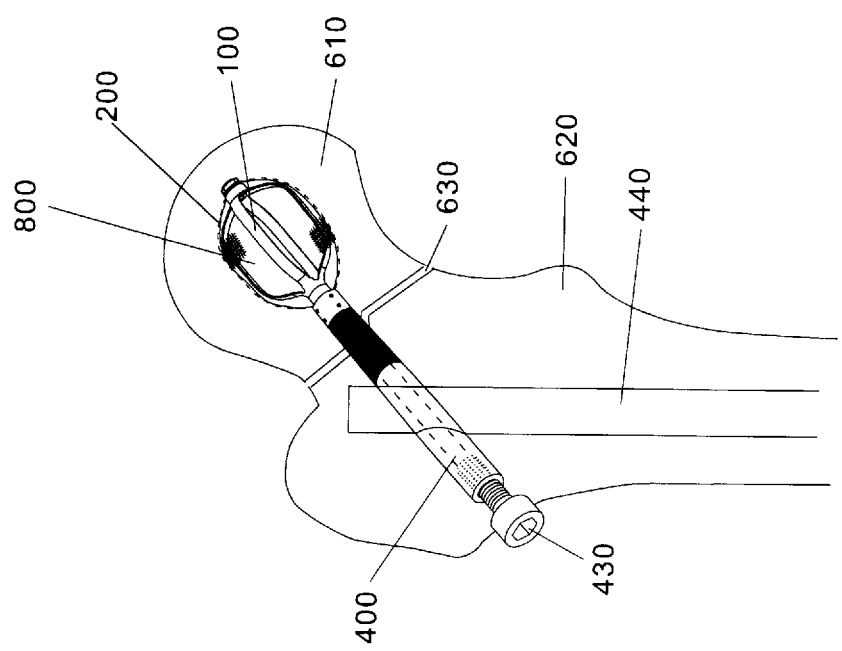
FIG. 15 is a perspective view illustrating a bone fixation system with the auxiliary fixing device according to the present invention applied to a hip joint.

FIG. 15 illustrates an embodiment for a bone fixation system with an auxiliary fixing device according to the present invention applied to a hip joint. The hollow fixing device 400, the expansion part 100, and the covering part 200 pass through a rear broken bone 620, a crack 630, a front broken bone 610 and an auxiliary fixing device 440. The front broken bone 610 and the rear broken bone 620 are joined to each other via injection of the medical filler 800; further, the pressing device 430 is utilized to unite the front broken bone 610, the rear broken bone 620, the hollow fixation device 400 and the auxiliary fixing device 440 more closely to enhance firmness thereof. Steps of surgery for bone fixation can be seen in FIGS. 16*a* to 16*k*.

Figure 16C:
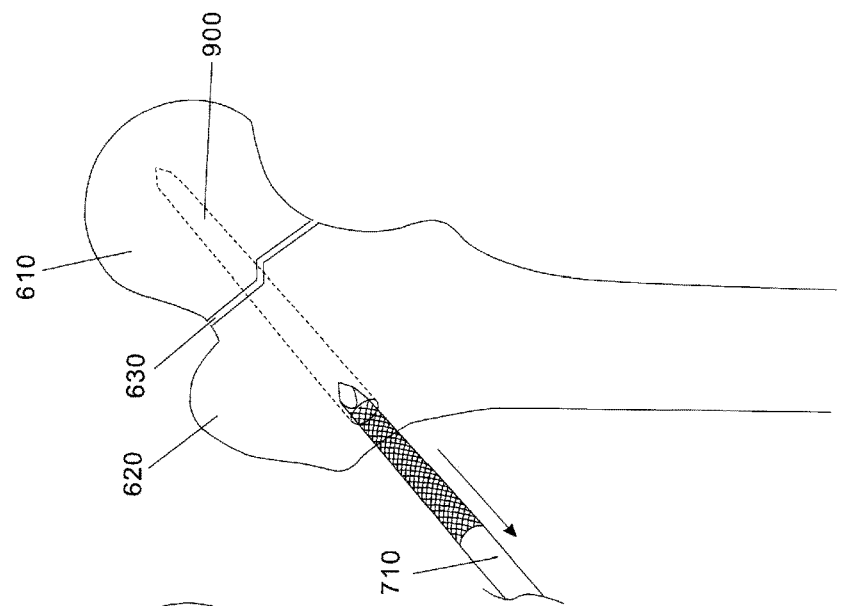
Figure 16B:
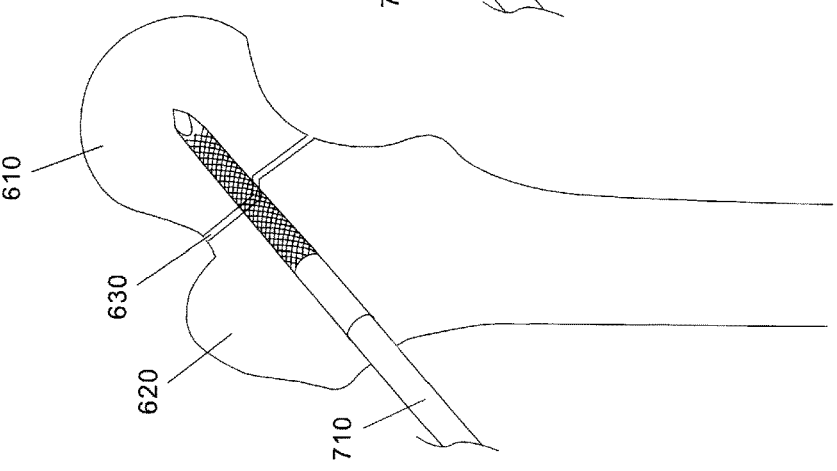
Figure 16A:
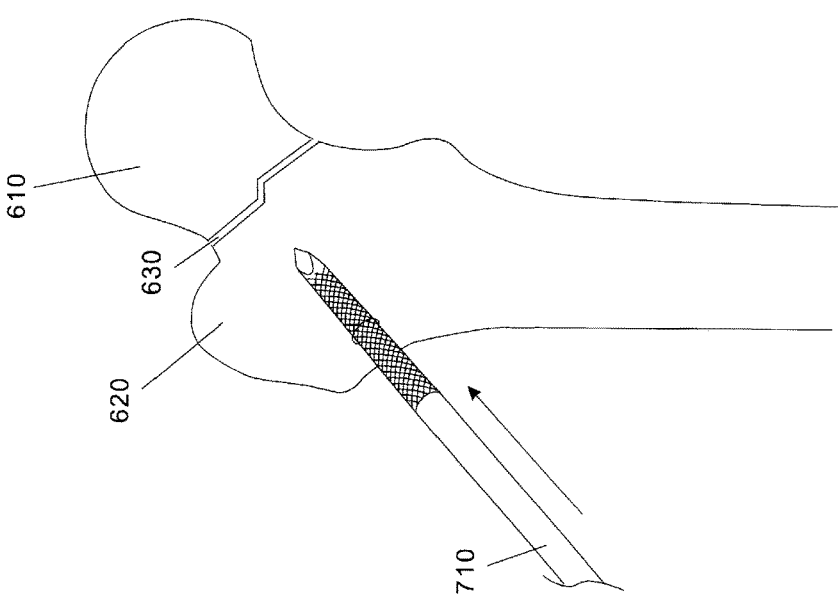
Figure 16D:
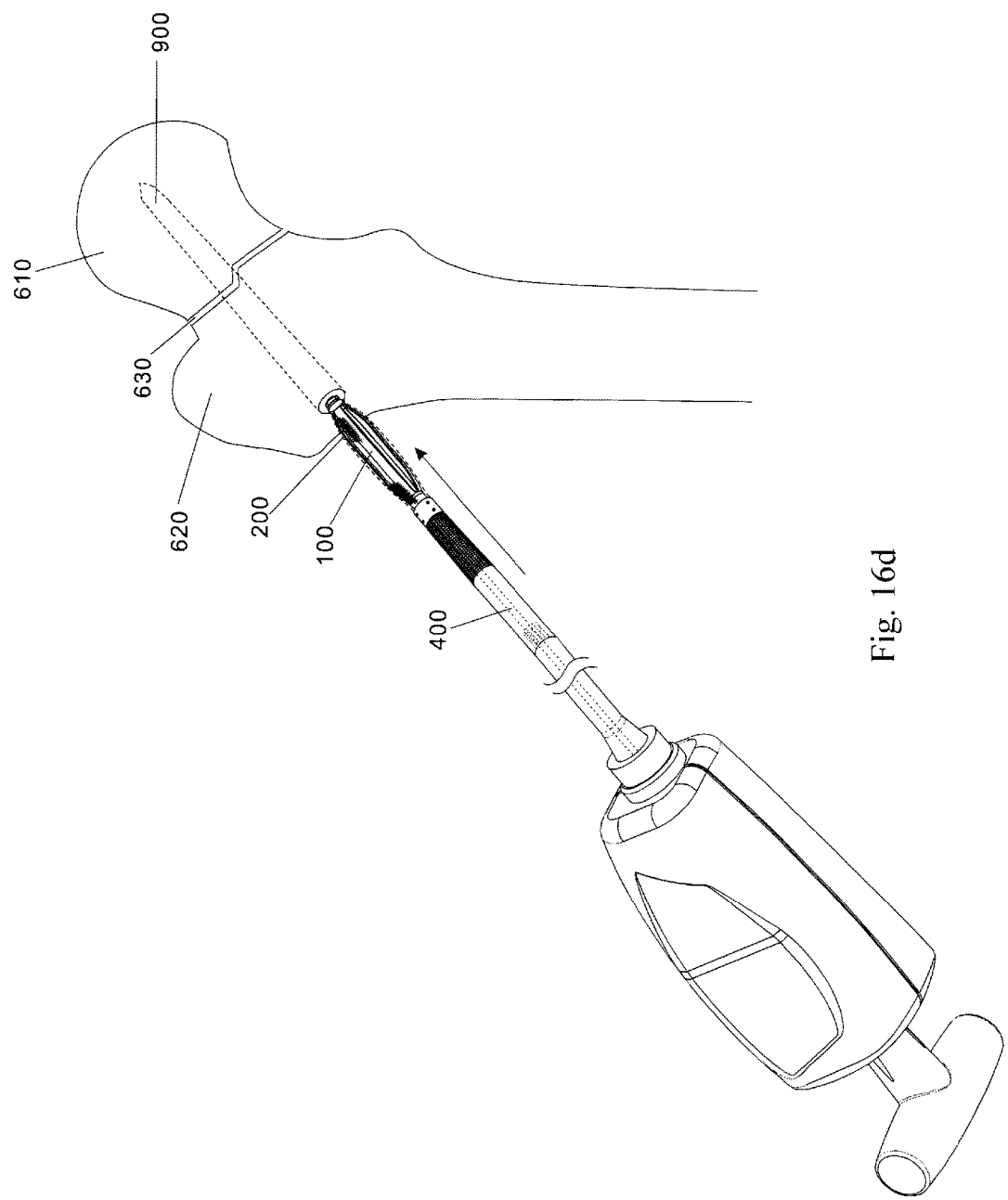
Figure 16E:
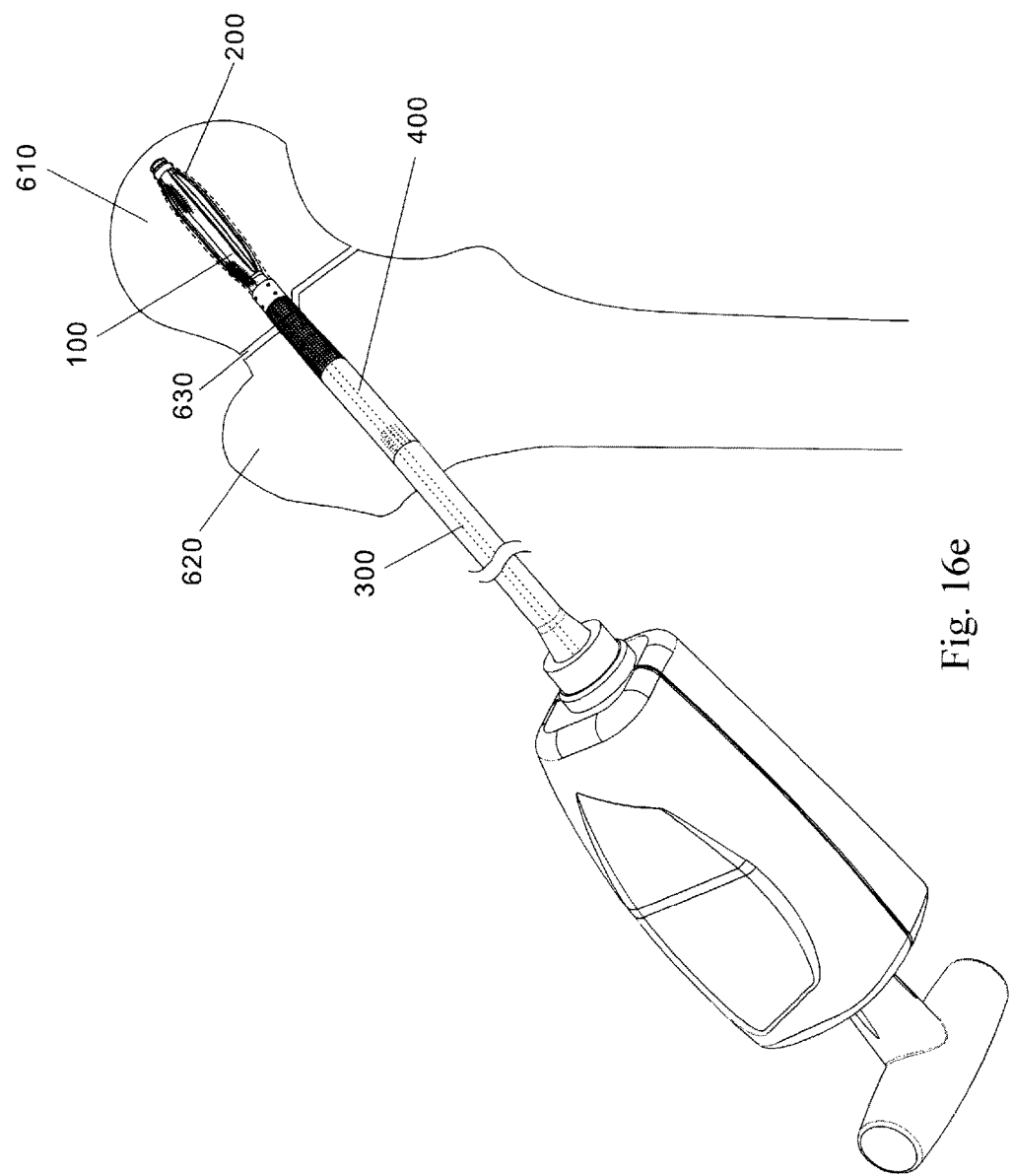
Figure 16F:
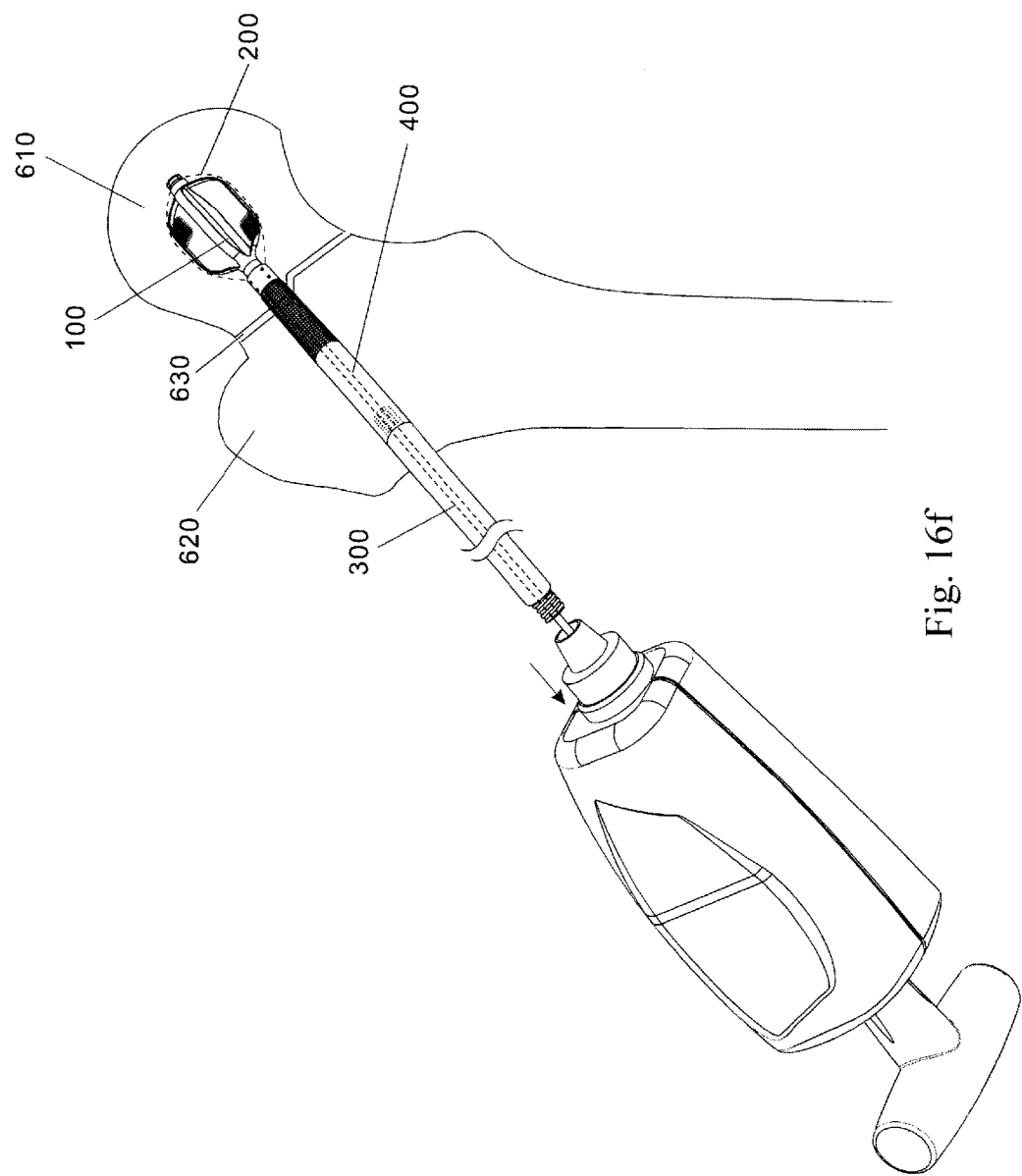
Figure 16G:
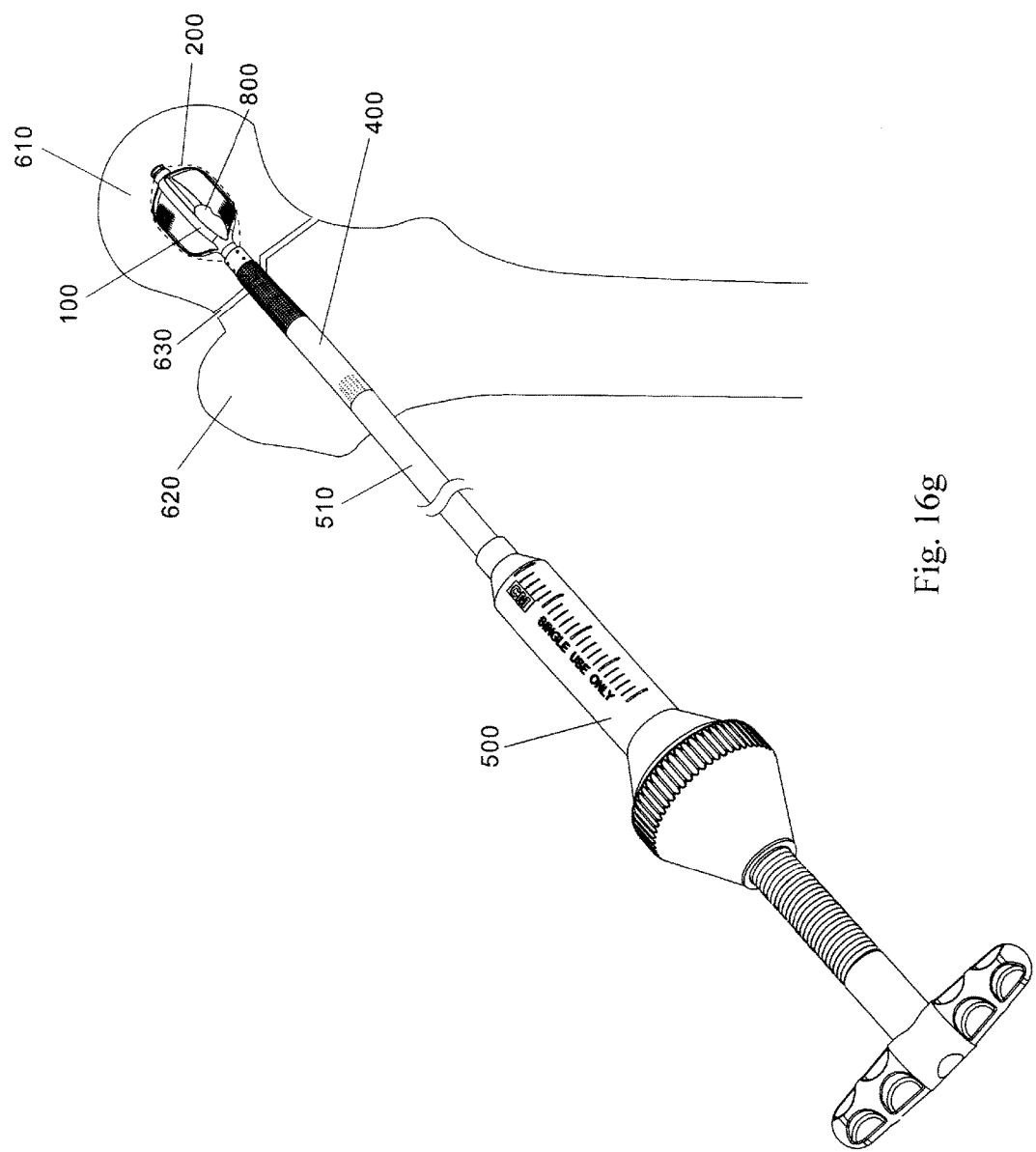
Figure 16H:
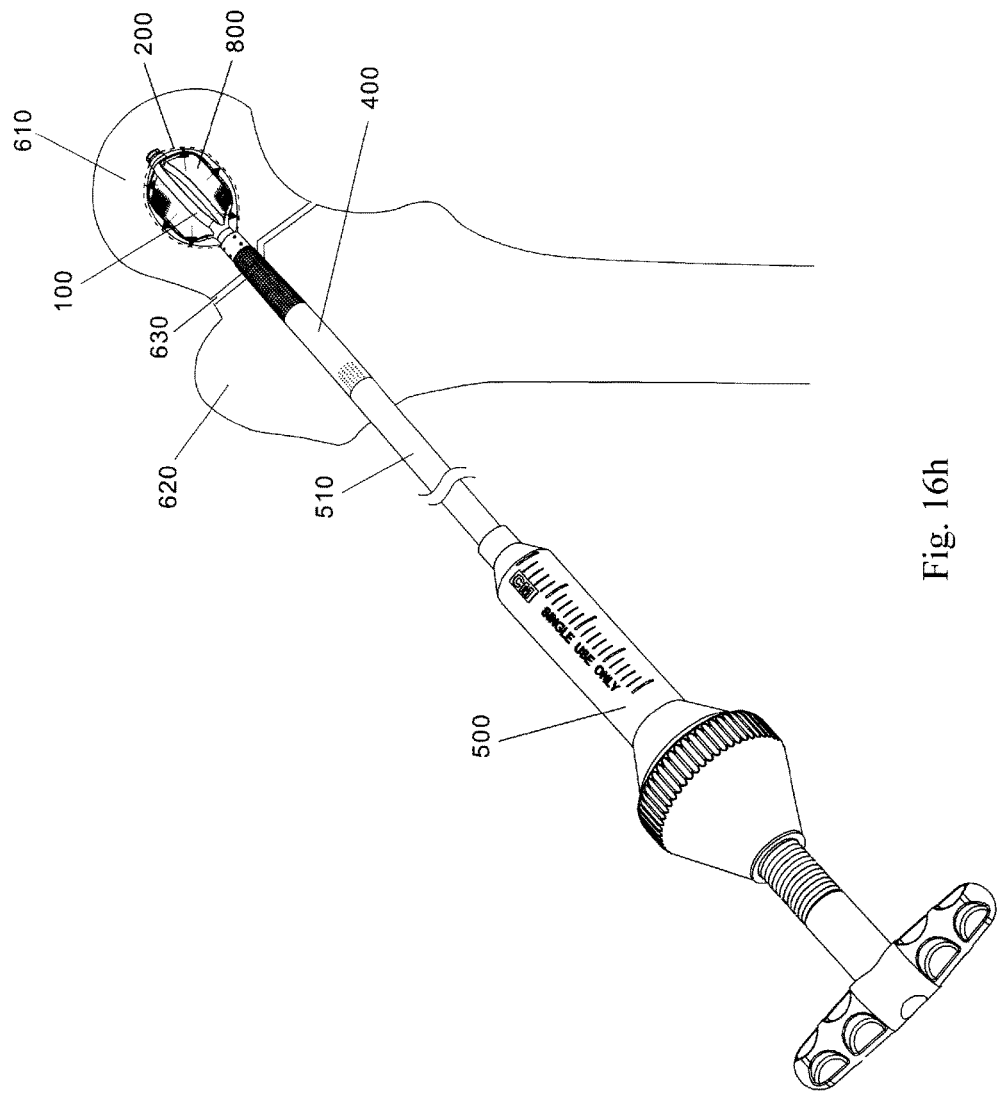

FIGS. 16*a* to 16*k* illustrate steps of surgery for a bone fixation system according to the present invention. FIG. 16*a* shows that a drill 710 drills into a rear broken bone 620. FIG. 16*b* shows that the drill 710 passes through the rear broken bone 620 and a crack 630 and enters a front broken bone 610. FIG. 16*c* shows that a hole 900 is generated after the drill 710 passes through the rear broken bone 620 and a crack 630 and enters a front broken bone 610, FIG. 16*d* shows that the hollow fixing device 400, the covering part 200 and the expansion part 100 are placed in the hole 900. FIG. 16*e* shows that the hollow fixing device 400, the covering part 200 and the expansion part 100 have been placed in the hole 900 completely. FIG. 16*f* shows that the expansion part 100 is in a state of expansion with the aid of the auxiliary expansion part 300. FIG. 16*g* shows that the auxiliary expansion part 300 has been replaced with an injection tool 500 and an extension tube 510 so as to inject the medical filler 800. FIG. 16*h* shows that the injection of the medical filler 800 is completed. FIG. 16*i* shows that the extension tube 510 is withdrawn from the hollow fixing device 400. FIG. 16*j* shows that a locking member 432 is employed to lock the pressing device 430 into the hollow fixing device 400. FIG. 16*k* shows that the pressing device 430 is locked in the hollow fixation device to press the connection between the front broken 610, the rear broken bone 620 and the hollow fixing device 400 closely.

Figure 17A:
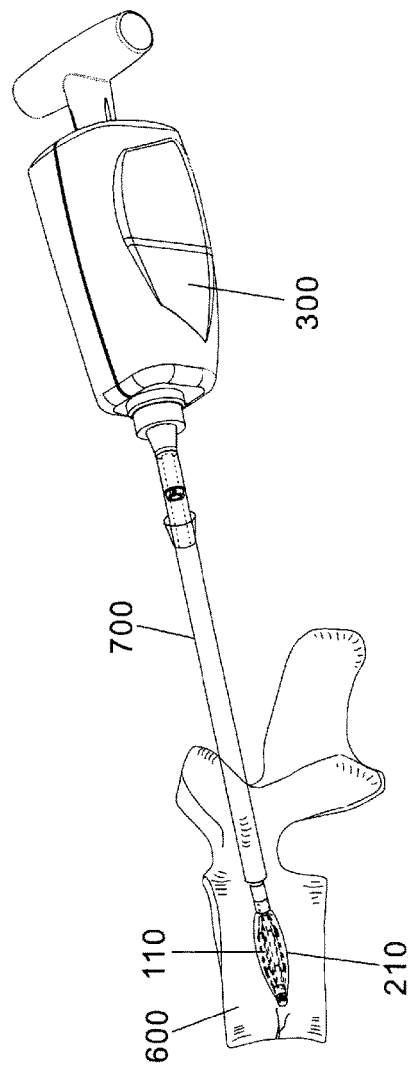
FIGS. 17a, 17b, 17c, and 17d are perspective views illustrating surgery steps of a device for bone fixation according to the present invention.
Figure 17B:
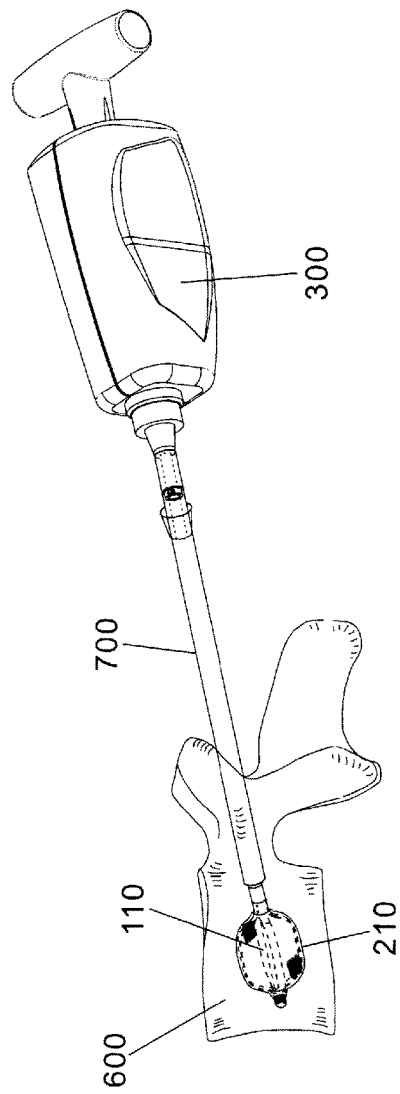
Figure 17C:
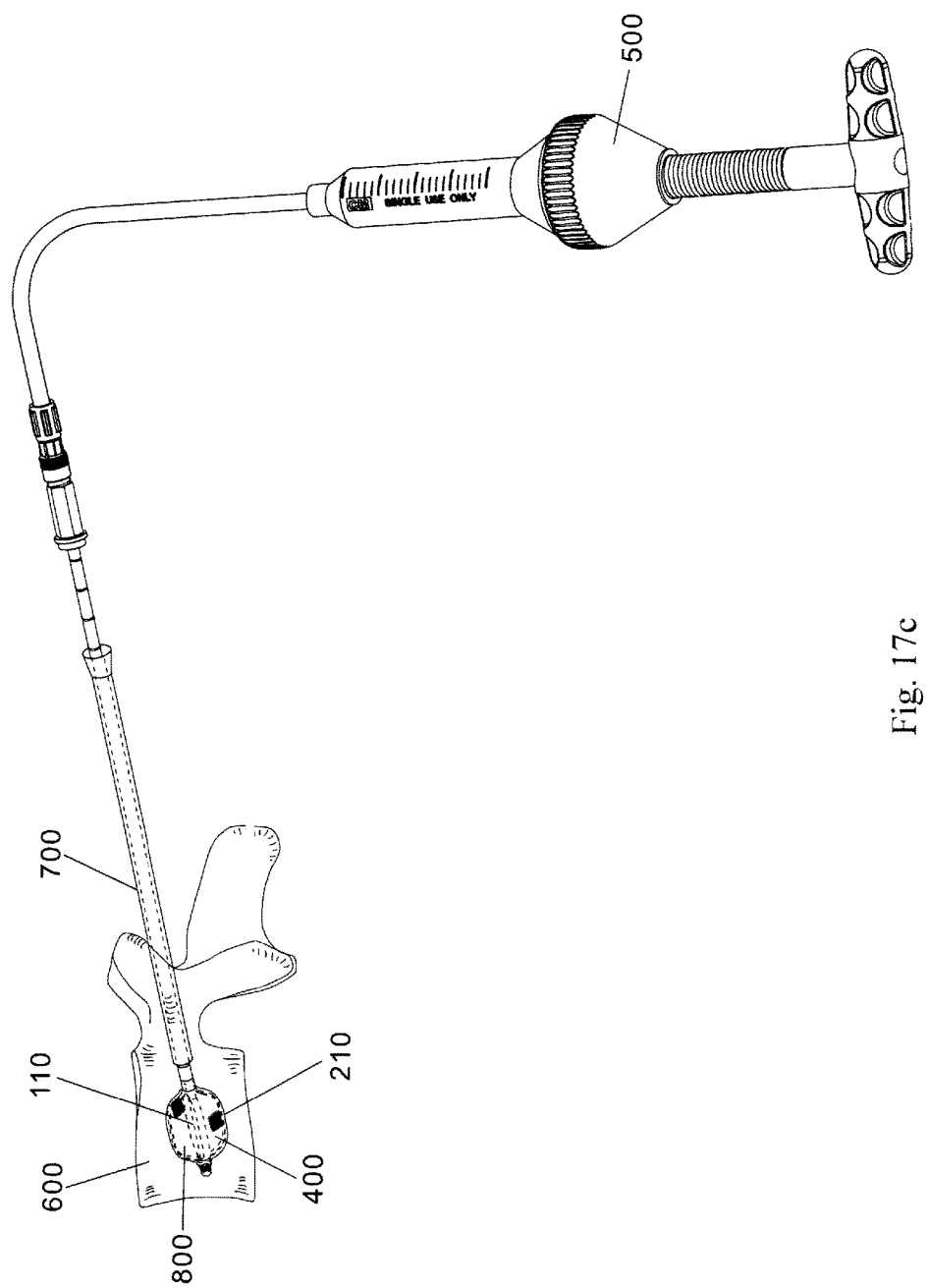
Figure 17D:
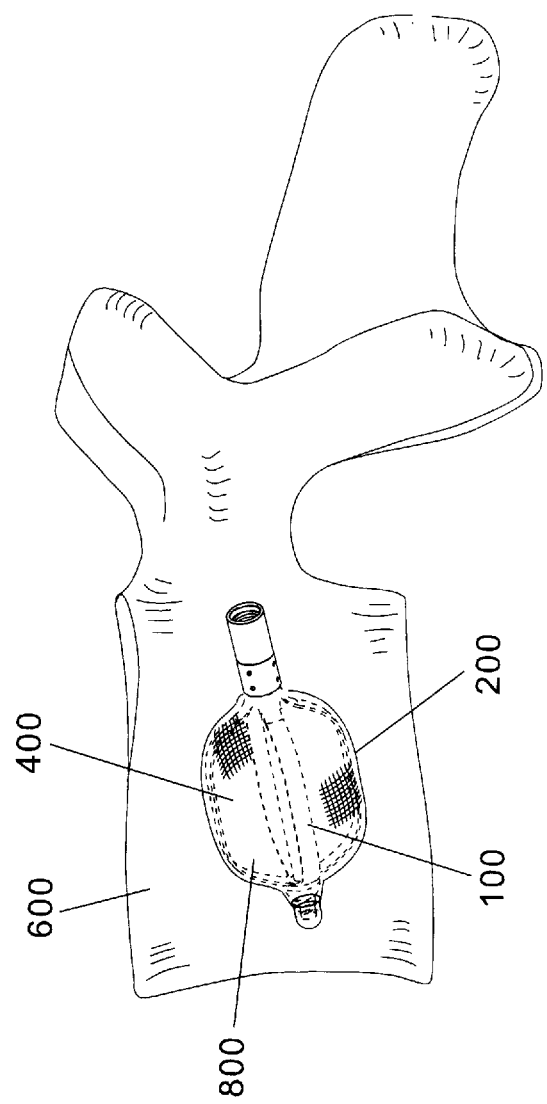

FIGS. 17*a*, 17*b*, 17*c*, and 17*d* illustrate steps of surgery for a device for bone fixation according to the present invention. FIG. 17*a* shows that the covering part 200 and the expansion part 100 are placed in a vertebra 600 via a tube 700. FIG. 17*b* shows that an auxiliary expansion part 300 is utilized to expand the expansion structure 110, and the expansion structure 110 props up the sphere-like covering member 210. FIG. 17*c* shows that the auxiliary expansion part 300 is replaced with an extension tube 500 and an injection tool 500 to perform injection of the medical filler 800. FIG. 17*d* shows that the device for bone fixation supports the vertebra 600 effectively after the injection of the medical filler 800 is completed.

What is claimed is:

1. A bone fixation system, comprising:
a device for bone fixation which comprises:
an expansion part having an end being a fixing end and another end being a top end, and having an expansion structure which is adjustable between an expanded state and a contracted state; and a covering part having an end being a front end and another end being a joining end, wherein said front end is joined to said top end, said joining end is secured to said fixing end, and said covering part covers said expansion part;

a hollow joining tube having a front end and a rear end, wherein the front end of the hollow joining tube is detachably joined to the fixing end of said expansion part;

an auxiliary expansion part having an end being a coupling end and another end being an operating end, wherein said coupling end is detachably joined to the rear end of said hollow joining tube;

an operation lever having an end being a front end, and another end being a rear end, wherein the front end of said operation lever is detachably joined to said expansion part, the rear end of said operation lever is joined to the operating end of said auxiliary expansion part, and said operation lever is capable of being operated to allow said auxiliary expansion part to adjust the expansion part in a state of expansion or a state of contraction;

an injection tool being joined to the rear end of said hollow joining tube or the rear end of said operation lever to inject or push a medial filler into said covering part via said hollow joining tube or said operation lever;

wherein said auxiliary expansion part is detached and said injection tool is attached after the auxiliary expansion part expands said expansion part with said operation lever for injecting or pushing the medical filler into the covering part.

2. The bone fixation system as defined in claim 1, wherein said expansion structure is a lantern-shaped expansion structure or a strip-shaped expansion structure.

3. The bone fixation system as defined in claim 1, wherein the top end of said expansion part has a protrusion, and the front end of said covering part has an extension member or a ring-shaped fixing member corresponding to said protrusion.

4. The bone fixation system as defined in claim 1, wherein the covering part is an elastic covering device, a web-shaped covering device, or a porous covering device.

5. The bone fixation system as defined in claim 1, wherein the front end of said covering part is cylinder-shaped, cone-shaped, sphere-like, gourd-shaped, or cube-like.

6. The bone fixation system as defined in claim 1, wherein said covering part is made from a material selected from the group consisting of poly-urethane, silicone and nylon.

7. The bone fixation system as defined in claim 1, wherein said covering part is made of biocompatible surgery sutures.

8. The bone fixation system as defined in claim 1, wherein said operation lever is hollow.

9. The bone fixation system as defined in claim 8, wherein said hollow operation lever has a hole at the front end thereof.

10. The bone fixation system as defined in claim 1, wherein the medical filler is a slurry.

11. A bone fixation system, comprising:
a device for bone fixation which comprises:
an expansion part having an end being a fixing end and another end being a top end, and having an expansion structure which is adjustably between an expanded state and a contracted state; and
a covering part having an end being a front end and another end being a joining end, wherein said front end is joined to said top end, said joining end is secured to said fixing end, and said covering part covers said expansion part;

wherein said expansion part and said covering part are placed in a bone, said covering part is expanded by expansion of said expansion structure;

a hollow fixing device having an end being an injecting end and another end being a connecting end, wherein the connecting end of the hollow fixing device is joined to the fixing end of said expansion part;

a pressing device being joined to the injecting end of said hollow fixing device;

an auxiliary expansion part having an end being a coupling end and another end being an operating end, wherein said coupling end is detachably joined to the injecting end of said hollow fixing device;

an operation lever having an end being a front end, and another end being a rear end, wherein the front end of said operation lever is detachably joined to said expansion part, the rear end of said operation lever is joined to the operating end of said auxiliary expansion part, and said operation lever is capable of being manipulated to allow said auxiliary expansion part to adjust the expansion part in a state of expansion or a state of contraction;

an injection tool with an end thereof being joined to the injecting end of said hollow fixing device or the rear end of said operation lever to inject or push a medical filler into said covering part via said hollow fixing device or said operation lever;

wherein said auxiliary expansion part is detached, said injection tool is attached instead after the auxiliary expansion part expands said expansion part with said operation lever for filling up the medical filler, the pressing device is set up after completing filling the covering part with the medical filler to press said device for bone fixation toward a bone at a surgical site.

12. The bone fixation system as defined in claim 11, wherein said expansion structure is a lantern-shaped expansion structure or a strip-shaped expansion structure.

13. The bone fixation system as defined in claim 11, wherein the top end of said expansion part has a protrusion, and the front end of said covering part has an extension member or a ring-shaped fixing member corresponding to said protrusion.

14. The bone fixation system as defined in claim 11, wherein the covering part is an elastic covering device, a web-shaped covering device, or a porous covering device.

15. The bone fixation system as defined in claim 11, wherein the front end of said covering part is cylinder-shaped, cone-shaped, sphere-like, gourd-shaped, or cube-like.

16. The bone fixation system as defined in claim 11, wherein said covering part is made from a material selected from the group consisting of poly-urethane, silicone and nylon.

17. The bone fixation system as defined in claim 11, wherein said covering part is made of biocompatible surgery sutures.

18. The bone fixation system as defined in claim 11, wherein said operation lever is hollow.

19. The bone fixation system as defined in claim 18, wherein said hollow operation lever has a hole at the front end thereof.

20. The bone fixation system as defined in claim 11, wherein the medical filler is a slurry.

21. The bone fixation system as defined in claim 11, wherein said pressing device is screws, or bone plates.

22. The bone fixation system as defined in claim 11, wherein said hollow fixing device has a stem embossed with ring-shaped, stripe-shaped, spot-shaped, or net-shaped pattern.

23. The bone fixation system as defined in claim 11, wherein said hollow fixing device has a stem with holes.

* * * * *